(12) United States Patent
Brockway et al.

(10) Patent No.: US 8,086,304 B2
(45) Date of Patent: Dec. 27, 2011

(54) PHYSIOLOGIC SIGNAL PROCESSING TO DETERMINE A CARDIAC CONDITION

(75) Inventors: Marina V. Brockway, Shoreview, MN (US); Vladimir V. Kovtun, Inver Grove heights, MN (US); Carlos A. Ricci, Apple Valley, MN (US)

(73) Assignee: Data Sciences International Inc., St. Paul, MN (US)

( * ) Notice: Subject to any disclaimer, the term of this patent is extended or adjusted under 35 U.S.C. 154(b) by 306 days.

(21) Appl. No.: 12/323,828

(22) Filed: Nov. 26, 2008

(65) Prior Publication Data

US 2009/0143692 A1 Jun. 4, 2009

Related U.S. Application Data

(60) Provisional application No. 60/991,650, filed on Nov. 30, 2007.

(51) Int. Cl.
*A61B 5/04* (2006.01)
(52) U.S. Cl. ...................................................... 600/515
(58) Field of Classification Search .................. 600/515, 600/509, 516
See application file for complete search history.

(56) References Cited

U.S. PATENT DOCUMENTS

| | | | |
|---|---|---|---|
| 4,678,987 A | 7/1987 | Bauck | |
| 5,148,812 A * | 9/1992 | Verrier et al. | 600/517 |
| 5,713,367 A | 2/1998 | Arnold et al. | |
| 5,842,997 A | 12/1998 | Verrier et al. | |
| 6,169,919 B1 | 1/2001 | Nearing et al. | |
| 6,236,882 B1 * | 5/2001 | Lee et al. | 600/509 |
| 6,449,592 B1 | 9/2002 | Das | |
| 6,453,191 B2 | 9/2002 | Krishnamachari | |
| 6,823,213 B1 * | 11/2004 | Norris et al. | 607/9 |
| 6,832,113 B2 | 12/2004 | Belalcazar | |
| 6,915,157 B2 | 7/2005 | Bennett et al. | |
| 6,983,183 B2 * | 1/2006 | Thiagarajan et al. | 600/509 |

OTHER PUBLICATIONS

Childers and Pao, "Complex demodulation for transient wavelet detection and extraction," *IEEE Transactions on Audio and Electroacoustics*, 20(4): 295-308.
Grace and Piti, "Quadrature sampling of high-frequency waveforms," *J. Acoust. Soc. Am.*, 1968, 44(5): 1453-1454.
Kodama et al, "Linkage between mechanical and electrical alternans in patients with chronic heart failure," *Journal of Cardiovascular Electrophysiology*, 2004, 15(3): 295-299.
Martinez et al., "Characterization of repolarization alternans during ischemia: Time-course and spatial analysis," *IEEE Transactions on Biomedical Engineering*, 2006, 53(4): 701- 711.
Nearing and Verrier, "Personal computer system for tracking cardiac vulnerability by complex demodulation of the T wave," *J Appl Physiol.*, 1993, 74(5): 2606-2612.
Shusterman and Goldberg, "Tracking repolarization dynamics in real-life data," *Journal of Electrocardiology*, 2004, 37: 180- 186.

* cited by examiner

*Primary Examiner* — Brian T Gedeon
(74) *Attorney, Agent, or Firm* — Fish & Richardson P.C.

(57) ABSTRACT

In a method for determining a cardiac condition, a sensed physiologic signal for a period of time including multiple cardiac cycles is received. Using the received physiologic data, a heart beat frequency to be used as a reference frequency is determined. A plurality of harmonics of the received physiologic signal is extracted based on the reference frequency, wherein the harmonics correspond to a plurality of alternans frequencies. Amplitudes of at least some of the extracted harmonics are determined, and are used to determine an alternans indicator value.

24 Claims, 13 Drawing Sheets

PHYSIOLOGIC SIGNAL PROCESSING TO DETERMINE A CARDIAC CONDITION

CROSS-REFERENCE TO RELATED APPLICATIONS

This application claims priority from U.S. Provisional Patent Application Ser. No. 60/991,650, filed on Nov. 30, 2007, and entitled "Physiologic Signal Processing To Determine A Cardiac Condition," the contents of which are hereby incorporated in their entirety by reference.

TECHNICAL FIELD

This disclosure relates to measuring cardiac electrical or mechanical instability and providing an assessment of cardiac disease progression.

BACKGROUND

Electrical alternans is a phenomenon that can be observed on an electrocardiogram (ECG) or electrogram recording as beat to beat alternation in the amplitude or morphology of electrocardiogram or electrogram waveforms. Electrical alternans was first recognized by H. Hearing in 1909 and was further characterized by Sir Thomas Lewis in 1910 as occurring in two instances: where the heart rate is fast, but the heart muscle is normal; or where the heart rate is normal, but the patient has a serious heart disease. Electrical alternans is a repolarization or conduction abnormality of the Purkinje fibers or myocardium. Typically alternans occur at elevated heart rates but the threshold heart rate can be lowered by various conditions like ionic disturbances or ischemia.

Repolarization alternans, also known as T-wave alternans (TWA), is defined as beat-to-beat fluctuations in amplitude, polarity or shape of a T wave of an electrocardiogram or electrogram signal. TWA has been associated with propensity to ventricular arrhythmias that result in sudden cardiac death. While seemingly unpredictable, ventricular arrhythmia is now recognized to exhibit features of a chaotic system en route from underlying instability to a disorganized pattern. In this progression, TWA that measure dispersion of recovery serve as a marker of cardiac instability.

Visible macroscopic TWA present in an ECG measured with surface electrodes have been associated with imminent onset of dangerous ventricular arrhythmias, and in some cases may leave limited time to intervene. Microvolt level TWA (mTWA) can be used to assess subtle changes in repolarization that occur far in advance of an arrhythmia. Microvolt level fluctuations in the T wave are not detectable by the unaided human eye, but can be revealed with computer analysis.

Mechanical alternans is a phenomenon of alternating strong and weak beats despite a constant heart rate. This phenomenon has been observed in patients with left ventricular dysfunction and seems to be related to risk for progressive heart failure. Mechanical alternans are often accompanied by electrical alternans.

SUMMARY

Devices, systems, and methods are described for measuring cardiac electrical or mechanical instability and providing an assessment of cardiac disease progression.

In a first general aspect, a method of determining a cardiac condition, includes receiving a sensed physiologic signal for a period of time including multiple cardiac cycles. The method also includes determining, using the received physiologic data, a heart beat frequency to be used as a reference frequency. The method further includes extracting a plurality of harmonics of the received physiologic signal based on the reference frequency, wherein the harmonics correspond to a plurality of alternans frequencies, and determining amplitudes of at least some of the extracted harmonics and using the amplitudes to determine an alternans indicator value.

In various implementations, the sensed physiologic signal may be an ECG signal. The harmonics may be extracted from a repolarization component of the ECG signal. The repolarization component may be a continuous repolarization component of the ECG signal. The alternans indicator value may be a T-wave alternans amplitude. Each of the plurality of harmonics may be fractional harmonics. The harmonics may include integer harmonics and fractional harmonics, and the harmonics may be extracted using one or more band pass filters. The method may also include assembling a blended signal comprising a sum of corresponding integer and fractional harmonics. The method may also include computing a complex envelope of the blended signal. The method may also include normalizing one or more powers of the extracted harmonics by a power of the noise band. The method may also include computing the alternans indicator value by taking the square root of a summation of powers of amplitudes of the extracted fractional harmonics. Alternans signal morphology may be reconstructed from the fractional harmonics. The sensed physiologic signal may be collected by an implanted device. The implanted device may collect the sensed physiologic signal using at least two electrodes positioned subcutaneously within a patient, or using at least one intracardiac electrode. The sensed physiologic signal may be telemetered from the implanted device to external processing equipment. The sensed physiologic signal may be analyzed within the implanted device. The physiologic signal may be an electrocardiogram or electrogram, and the alternans indicator value may be a QRS alternans value. The method may also include triggering a sensed change of the physiologic signal in response to a change in heart rate. The method may also include issuing a warning in response to comparing the alternans indicator value to the predetermined threshold value. Input noise associated with the sensed physiologic signal may be measured, and at least a portion of the sensed physiologic signal may be rejected if the measured noise exceeds a predetermined threshold. The method may also include comparing the alternans indicator value to a predetermined threshold value and storing a result of the comparison in an electronic storage location.

In a second general aspect, a system includes an electrode configured to sense a physiologic signal of a patient for a period of time including multiple cardiac cycles. The system also includes a processor module programmed to receive the sensed physiologic signal, determine, using the received physiologic data, a heart beat frequency to be used as a reference frequency, extract a plurality of harmonics of the received physiologic signal based on the reference frequency, where the harmonics correspond to a plurality of alternans frequencies, and determine amplitudes of at least some of the extracted harmonics and use the amplitudes to determine an alternans indicator value.

In various implementations, the sensed physiologic signal may be an ECG signal.

The details of one or more implementations are set forth in the accompanying drawings and the description below. Other features, objects, and advantages will be apparent from the description and drawings, and from the claims.

BRIEF DESCRIPTION OF DRAWINGS

Like reference symbols in the various drawings indicate like elements.

DETAILED DESCRIPTION

Figure 1:
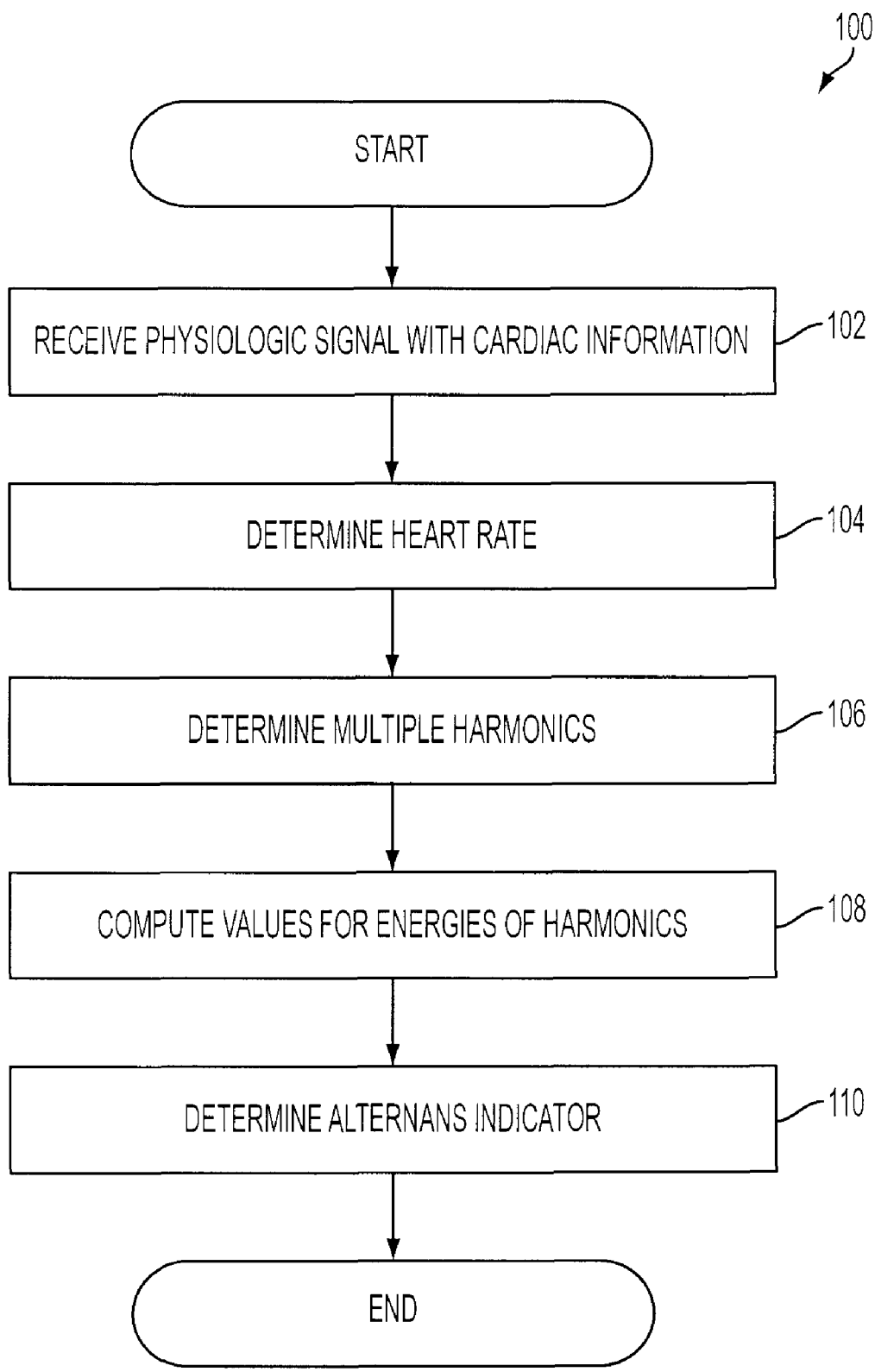
FIG. 1 is a flow chart of an exemplary process that can be used to determine an alternans indicator from a physiologic signal.

This document describes methods, systems, and devices that can be used to accurately measure small changes in a physiologic signal of a patient that can indicate cardiac instability. The physiologic signal can be analyzed using a time-frequency analysis technique that uses harmonic decomposition to analyze portions of interest in the physiologic signal. Harmonic decomposition may be used to isolate components of the physiologic signal that may provide improved risk information relating to cardiac instability, which may permit better assessments of a patient's cardiac state. The methods described here may provide additional information on the morphology of cardiac instability dynamics, which might be correlated to instability origin, ion imbalance or ischemia location.

According to some implementations, the physiologic signal includes cardiac information, or is associated with the patient's cardiac cycle, and may be analyzed to determine a risk indicator value, such as an alternans indicator value, for the patient. The risk indicator value may indicate a patient's susceptibility to a serious cardiac condition, such as sudden cardiac death. As will be described below, many types of physiologic signals may be analyzed using the techniques described here, including electrical and mechanical signals, and many types of devices or systems can be used to measure and analyze such signals, including one or more implanted devices within the patient, one or more external devices, or some combination of the above. Because the techniques described herein may accurately detect even very small changes in portions of the physiologic signal, and may do so in a computationally efficient manner, improved assessments of a patient's cardiac condition may be obtained, which may lead to prevention or postponement of a serious cardiac event or condition for the patient, according to some implementations. Also, the computationally efficient techniques described here may be implemented in implantable devices without unduly affecting the device's battery life, according to some implementations, which may provide flexible monitoring solutions and increase the likelihood that adverse cardiac events can be predicted and avoided.

Periodic variability in a physiologic signal that includes cardiac information can serve as a marker of cardiac instability, which can lead to arrhythmia in the presence of a trigger. For example, ventricular tachycardia is an arrhythmia that can progress to ventricular fibrillation, an example of chaotic behavior. Ventricular fibrillation can lead to sudden cardiac death. A health care professional can use the methods, systems, and devices described in this specification to assess patient risk of sudden cardiac death or other cardiac pathologies. In some implementations, the methods, systems, and devices can be used to show linkages in risk factors of various patient histories, and can be used to assess risk factors in individual patients.

Various physiologic signals or portions of physiologic signals may be analyzed to determine a cardiac state or determine a risk indicator relating to a patient's cardiac stability. For example, the methods disclosed herein may be used to analyze electrical signals or mechanical signals that carry information relating to a patient's cardiac cycle. One type of periodic variability that can be detected using the techniques discussed herein may be referred to as "alternans" of the physiologic signal or a portion of the physiologic signal. For example, an alternans signal in a 2:1 pattern (i.e., ABABAB . . . ) can be measured at a frequencies that are multiples of one half of the heart rate. In some implementations, the physiologic signal can be an ECG signal, or a portion of an ECG signal. For example, the method can be used to analyze an ECG signal, and specifically the T-wave or repolarization wave of the ECG signal, to determine if a patient exhibits T-wave alternans, a periodic variability associated with the T-wave of the ECG signal. In another example, the method can be used to analyze another portion of the ECG signal, the QRS complex, to detect QRS alternans associated with the QRS complex, which may also be used to determine the patient's risk of sudden cardiac death. In other implementations, the method can be used to analyze a mechanical signal. For example, a patient's blood pressure signal may be measured, and included in the signal may be a mechanical alternans signal that can be analyzed to determine risk of sudden cardiac death.

FIG. 1 is a flow chart of an exemplary process 100 that can be used to determine an alternans indicator from a physiologic signal. In various implementations, the process 100 may be executed by one or more implantable devices within a patient, by one or more devices or systems external to the patient, or by some combination of the above. In some cases, portions of the process 100 may be executed by an implantable device, while other portions of the process 100 may be executed by one or more external devices. The process 100 generally involves receiving the physiologic signal with cardiac information, determining a heart rate from the physiologic signal, determining multiple harmonics from the signal, computing values for energies of the harmonics, and determining a risk indicator or a risk assessment for the patient.

At an initial step 102, a physiologic signal with cardiac information is received. In various implementations, any physiologic signal that includes information relating to a patient's cardiac cycle may be received and analyzed for indications of a cardiac anomaly. The physiologic signal may be an electrical signal or a mechanical signal. In some implementations, the physiologic signal can be an ECG or electrogram signal. In other implementations, the signal can be a mechanical signal, such as a mechanical pulsus signal. In other implementations, the received signal can be a portion or a component of the above signals. As described further below, the signal can be received following various triggers. Also, a device may measure the signal, receiving the signal from one or more sensors or electrodes in communication with the device, according to some implementations. For example, if an electrical signal such as an ECG or electrogram is measured, two or more electrodes may be used to sense the heart's electrical activity. If a mechanical signal is measured, one or more sensors may sense the signal. In some implementations, the signal may be received by a device from another device, such as over a wired or wireless communication channel.

Next, at step 104, a heart rate can be determined using the received physiologic signal. The heart rate can be determined by analyzing a recurring periodic feature of the signal, where the recurring periodic feature corresponds to a portion of the patient's cardiac cycle. For example, the frequency of the QRS complex can be used to determine a heart rate frequency. The heart rate frequency can be used as a reference frequency or central frequency for harmonic decomposition. In some implementations, ectopic or uncorrelated heart beats can be removed from the physiologic signal, as they may adversely affect the process. An ectopic beat can be described as a cardiac beat originating elsewhere than at the sinoatrial node, causing the beat to be represented "out of place" with respect to other beats in the physiologic signal. An uncorrelated beat can be described as a beat that has morphology different from other beats in the sequence. As described further below, the proportion of ectopic beats in the signal can also be determined, which may be used to further assess the quality of the measured physiologic signal.

Next, multiple harmonics can be determined (106). For example, an integer harmonic and a fractional harmonic (one integer-fractional harmonic pair) may be determined. Alternatively, two or more integer-fractional harmonic pairs may be determined. In some implementations, only fractional harmonics may be determined. In some implementations, one or more harmonics of interest in the physiologic signal or in a portion of the physiologic signal may be identified for analysis. As such, analysis may be focused on the portions or components of the physiologic signal that may yield more relevant cardiac risk information, without expending processing or analytic resources analyzing portions or components of the physiologic signal that may yield minimal or no information relating to cardiac instability, and which may obscure information present in the portions or components of interest. In some implementations, a technique that can be used to extract this information is a modification of subband coding with bands centered at multiples of heart rate frequency. Harmonics of the signal may be calculated in a number of ways, including using a band-pass filter centered around a harmonic frequency or filtering integer harmonics to suppress energy of the fractional harmonics and successively subtracting the integer harmonics. Information associated with the harmonics can be used to obtain a more accurate risk assessment value for the patient.

Fractional harmonics can be described as harmonics at frequencies that are multiples of one-half of the heart rate frequency, called the central frequency. In some implementations, frequency bands that span harmonics of the central frequency can be determined using heart rate frequency information. In some implementations, integer-fractional harmonic pairs may be extracted. Integer-fractional harmonic pairs may be determined in iterative fashion, according to some implementations. In some implementations, the process 100 can use a filter bank to determine the integer-fractional harmonic pairs. For example, a first band-pass filter in a combination can be centered on the fractional harmonic, and a second band-pass filter in the combination can be centered on the integer harmonic. In another implementation, the first integer harmonic and the first fractional harmonic can be extracted with one dual bandpass filter, which can be a convolution of the two filters including both pass bands. The harmonic pairs can be added together to create a blended signal, according to some implementations. In some implementations, a blended signal may comprise a single integer-fractional harmonic pair.

In some implementations, a signal corresponding to the integer-fractional harmonic pair can be subtracted from the physiologic signal, leaving a residual signal (i.e., the input signal minus the harmonic pair). A next integer-fractional harmonic pair can then be extracted from the residual signal. In this fashion, iterative extraction of fractional harmonics or integer-fractional harmonic pairs from the base signal may be performed to obtain a harmonic set of interest for analysis. For example, three such extractions may be performed in succession to obtain the first, second and third fractional harmonics, corresponding respectively to frequency multiples of 0.5, 1.5, and 2.5 or the heart rate. In other examples, additional or fewer fractional harmonics may be determined, such as a fourth fractional harmonic, a fifth fractional harmonic, etc. Some simpler implementations may only determine the first fractional harmonic for analysis, or perhaps the first and second fractional harmonic. These steps can continue until all desired fraction harmonics or integer-fractional harmonic pairs are determined. In other implementations, filtered integer-harmonic pairs can be extracted using a phase-lock loop. Each integer-fractional harmonic pair can be added together to create a blended signal.

In some implementations, a complex envelope may be computed from the blended signal. In some implementations, the blended signal can be cleaned to remove phase anomalies prior to computation of the complex envelope. In some implementations, the blended signal can be compressed by sampling at fiducial points, and its envelope may be computed by interpolating over peaks of the signal for amplitude maximums values and valleys of the signal for amplitude minimum values. The process 100 can then perform amplitude demodulation to separate the fractional harmonic or harmonics and the noise band. For example, a linear-phase band-pass filter can be used to extract baseline noise from the signal.

At step 110, a risk indicator, such as an alternans indicator value, may be determined that is indicative of a patient's susceptibility to a cardiac event or condition. The risk indicator may be determined in a number of ways. As one example, a root mean square operation may be used in the determination. For example, the fractional harmonic powers, as determined in step 108, can be added and the square root of the sum computed. The risk indicator may be stored in an electronic storage location, according to some implementations. In some implementations, the risk indicator can be compared to a threshold value. In various implementations, the threshold value may be a predefined constant, or may represent a value that is modified over time, for example. The risk indicator may be dynamically tracked over time, which may provide advantageous visibility into a patient's cardiac risk profile, and may permit detection of risk indicators that would likely be missed using techniques that do not dynamically track. In some implementations, determination of the risk indicator includes consideration of underlying factors such as an onset heart rate for the alternans.

In one example, the process 100 can be used to determine an alternans indicator from a mechanical signal, such as a mechanical pulsus signal. If the alternans indicator exceeds a threshold, such as a mechanical pulsus or other threshold, the patient may be at a high risk of sudden cardiac death. In other implementations, an electrical signal, such as an ECG signal or a portion of the ECG signal (e.g., a continuous repolarization signal comprising T-waves extracted from the ECG signal), may be analyzed. In some implementations, the patient, a health care professional, or both, can be notified of a heightened risk of an adverse cardiac event or condition, as indicated by the alternans indicator computed as described above. In other implementations, the alternans indicator can be used later to compare to other risk indicators. For example, in implementations where T-wave alternans are detected, the health care professional can use the data over a period of time to determine if the patient exhibits a pattern of T-wave alternans.

As mentioned above, the physiologic signal can be received following various triggers. Examples of triggers can include a periodic timing signal that triggers sampling of the physiologic signal at regular predetermined intervals, such that the signal may be received. In this fashion, the signal may be received in asymptomatic fashion over a period of time, such as over several weeks or months, or over a year or more. A health-care professional can look for trends in the data over a period of time. In other implementations, the signal can also be received in symptomatic fashion, as in response to a request by the patient or the health care professional, or in response to a detected physical event or indication. In still other implementations, the signal can be received if the patient is experiencing changes in other physiologic signals, to list just a few examples.

As described above, the signal can be received from various sources. In some implementations, receipt of the signal can be by an implanted device, as by sampling the physiologic signal using one or more sensors or electrodes in communication with the device. The sensors or electrodes may be, without limitation, attached to one or more leads (e.g., intra-cardiac, subcutaneous, intra-vascular, etc.) connected to the device, or associated with a port or exterior surface of the device. For example, electrogram signals may be measured using intra-cardiac leads attached to an implanted device, a subcutaneous ECG signal may be measured by a device implanted subcutaneously in a patient and in communication with electrodes to measure the subcutaneous ECG signal, or the device may be in communication with a pressure measurement port that can measure pressure within an or outside an organ (e.g., heart or vasculature, etc.), to list just a few examples. In other implementations, receipt of the signal can be by an external device, as by sensing the signal using external sensors or electrodes (e.g., electrodes externally attached to a patient's skin), or receiving the signal over a communication channel (e.g., by wireless telemetry, over a wired or wireless communication network, etc.). In one implementation, an implanted device may be implanted subcutaneously within a patient, and one or more sensors or electrodes in communication with the device may sense or receive the signal. In other implementations, the implanted device may be implanted within or exterior of an organ of the patient. The sensors or electrodes may be, in various implementations, located exterior to the patients heart or interior to the patient's heart. In other cases, the sensors or leads may be external to the patient, and one or more external devices may be used. In other implementations, the signal can be received from an implanted device in the subcutaneous layer of the patient. In still other implementations, the signal can be received from an external device.

In some implementations the process 100 can benefit from determining ectopic or uncorrelated beats in the signal, or the proportion of such beats in the signal. Because ectopic and uncorrelated beats can corrupt the data set, it can be advantageous to identify these beats to remove them from the data set or to assess whether sufficient uncorrupted data remains in the set to yield acceptable results. In some implementations, if the proportion of ectopic beats in a signal exceeds a predetermined threshold, the process 100 can determine that an insufficient amount of uncorrupted data remains in the data set, and may discontinue the process 100. In other implementations, if a sufficiently high proportion of ectopic or uncorrelated beats are identified, an alert indicating a chaotic state may be issued.

Figure 2:
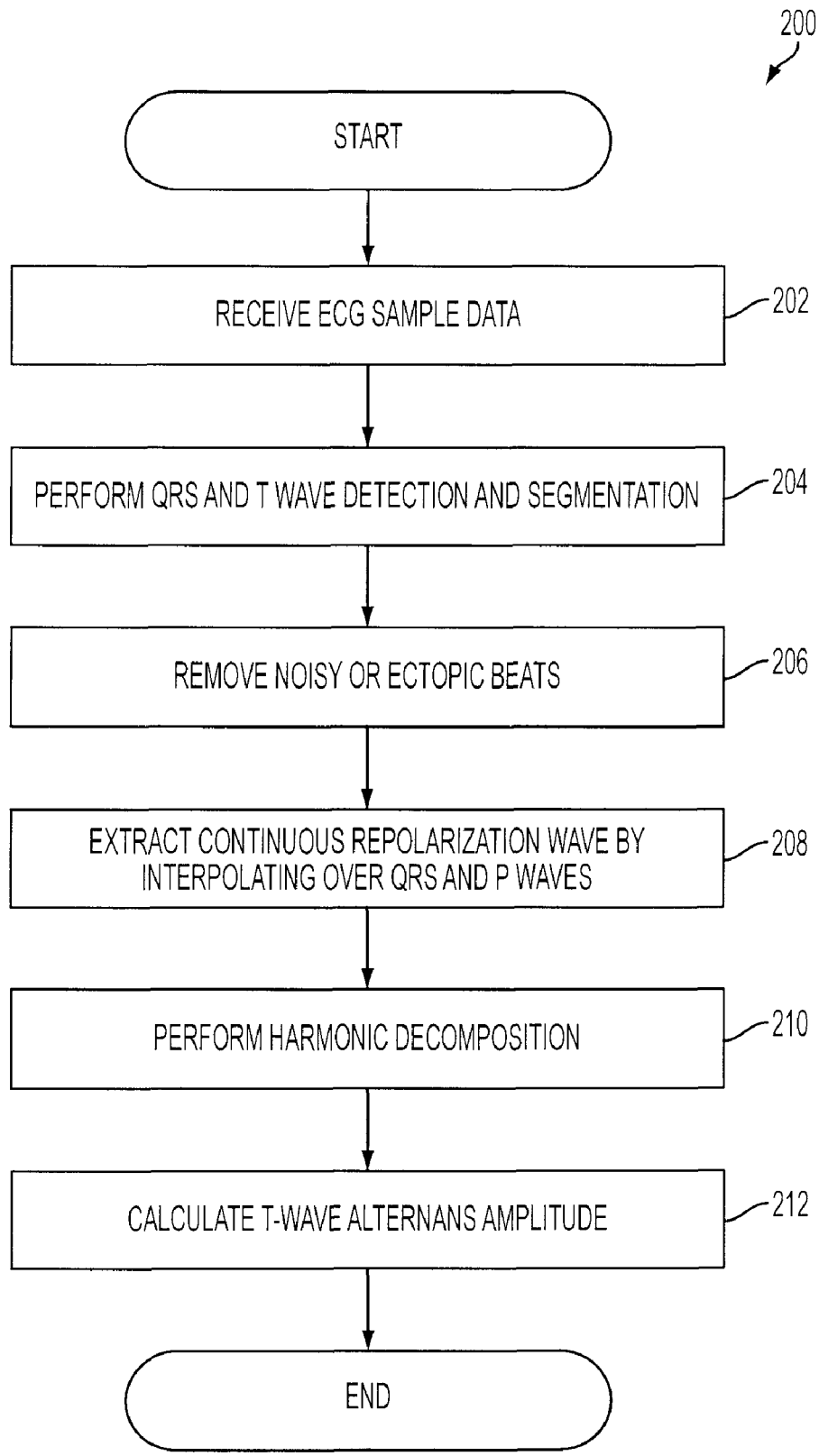
FIG. 2 is a flow chart of an exemplary process that can be used to determine a T-wave alternans risk indicator from an ECG signal.

FIG. 2 is a flow chart of an exemplary process 200 that can be used to determine a T-wave alternans risk indicator from an ECG signal. A T-wave alternans risk indicator may be determined to assess a patient's risk for sudden cardiac death or other cardiac anomalies, according to some implementations. The process 200 generally involves receiving ECG sample data, performing QRS and T wave detection and segmentation, removing uncorrelated or ectopic beats, extracting a continuous repolarization wave by interpolating over QRS and P waves, performing harmonic decomposition, and estimating a T-wave alternans amplitude.

At an initial step 202, ECG sample data may be received. The ECG signal may be sampled or received at any appropriate frequency. For example, the ECG sample data can be received at an 800 Hz frequency and then downsampled at 200 Hz, but other frequencies could similarly be used. In some implementations, the ECG sample data can contain a predetermined number of beats or be of predetermined length of time. For example, the ECG sample data can include 128 beats, but other appropriate numbers of beats may be used, such as 32, 64, 256, 512, and others. In some implementations, the ECG sample data can be received until a predetermined number of "clean" beats, or beats that are not uncorrelated or ectopic, are received, as will be described further below.

QRS complex and T wave detection and segmentation (204) can then be performed, according to some implementations. For example, in a normal heartbeat, the QRS complex contains the highest voltage level, and the T wave may be located within the ECG signal after first locating the QRS complex, or some portion of the QRS complex, such as the R wave.

Next, uncorrelated or ectopic beats can be removed (206). In some implementations, each QRS complex is analyzed to determine whether or not it is correlated to others. An uncorrelated QRS complex may reflect changes in electrical conduction during depolarization. Such a change may be likely to translate to changes in repolarization that obscure the TWA signal. In various implementations, this step 206 may be optional, and the process may proceed directly from performing QRS and T wave detection and segmentation 204 to step 208.

A continuous repolarization wave can then be extracted from the ECG signal by interpolating over QRS and P waves of the ECG signal (208). This may permit later analysis to focus on a portion of the ECG signal, the T-wave, that may be of particular interest for cardiac state determination. In some implementations, the process 200 can determine the continuous repolarization wave using discrete data points. In some implementations, the points used for interpolation can be a midpoint between the end of the T wave and the start of the P wave, and the QRS onset. In this fashion, a signal of continuous T waves, representing successive T waves from a continuous ECG signal, may be obtained from an input ECG signal. The terms "repolarization wave" and "T wave" may be used interchangeably herein, and refer to the portion of the ECG wave or cardiac cycle associated with ventricular repolarization.

At step 210, harmonic decomposition of the continuous T-wave signal may be performed. Harmonic decomposition may be performed using any of the methods described above with reference to FIG. 1. In one example, frequency bands that span harmonics of the heart rate frequency are located. In some implementations, filtered integer-fractional harmonic pairs are extracted. Extracting integer harmonics may be desirable, for example, so as to remove the generally higher energies from the signal associated with the integer harmonics, such that analysis may be focused on fractional harmonics of interest. For example, integer-fractional harmonic pairs may be iteratively determined by considering successive (first, second, third, etc.) integer-fractional harmonic pairs. In some implementations, a filter bank consisting of a collection of filters can be used to determine the integer-fractional harmonic pairs. For example, a first band-pass filter or passband region can be chosen to center on a fractional harmonic frequency and a second band-pass filter or passband region can be chosen to center on an integer harmonic frequency. Using this example, the first integer harmonic and the first fractional harmonic can be extracted with one filter, which can be a convolution of the two filters including both pass bands.

In other implementations, a signal corresponding to the integer-fractional harmonic pair can be iteratively subtracted from the physiologic signal and stored for analysis, leaving a residual signal. A next integer-fractional harmonic pair can then be extracted from the residual signal and stored, leaving a further reduced residual signal. If desired, additional integer-fractional harmonic pairs can be extracted from the residual signal remaining at each step in iterative fashion. These steps can continue until a desired number of integer-fractional harmonic pairs are determined. In still other implementations, filtered integer-harmonic pairs can be extracted using a phase-locked loop. In some implementations, the fractional-harmonic pair can be added together to form a blended signal.

A T-wave alternans amplitude can then be calculated (212). The amplitude of the T-wave alternans may depend on a magnitude of the T-wave. T-wave alternans amplitude values may be estimated in a number of ways. For example, in various implementations, amplitudes may be estimated directly, as from a demodulated complex envelope of the blended integer and fractional harmonic signals; in other implementations, first powers of the fractional harmonics may be added, and then a square root of the sum taken. Regarding harmonic power computation, each fractional harmonic can be multiplied by its conjugate to determine the harmonic's power, according to some implementations. Then, TWA amplitude may be estimated, for example by taking a square root of a sum of the fractional harmonic powers. This may provide a root-mean square estimation of TWA amplitude. In some implementations, the power of the noise band can be estimated and used to adjust TWA amplitude.

Figure 3:
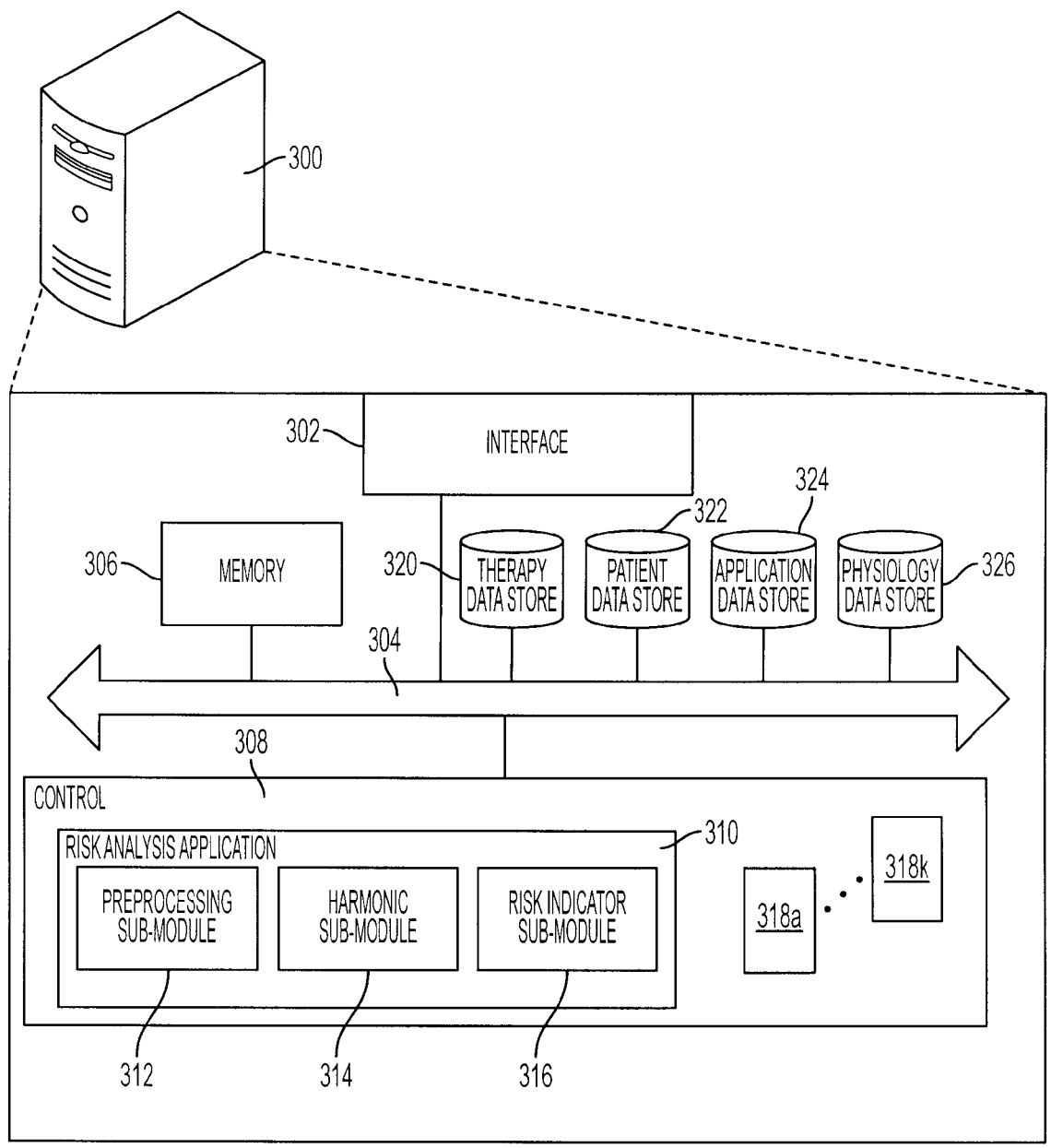
FIG. 3 is a block diagram of an exemplary system that can be used to analyze received physiologic signal data with cardiac information.

FIG. 3 is a block diagram of an exemplary system that can be used to analyze received physiologic signal data with cardiac information. The depicted implementation shows a server 300 that can implement techniques disclosed herein, but in other implementations the techniques may be executed by an implanted device, or by another type of external computing device, such as a handheld computing device (e.g., PDA, mobile phone, smartphone, etc.) or a personal computer. In general, the server 300 receives the physiologic signal data, determines a heart rate from the physiologic signal, and uses harmonic decomposition techniques to determine harmonic components of the physiologic signal to determine a cardiac risk indicator value for a patient. In some cases, portions of the system may be executed in an implanted device, while other portions may be executed by one or more external devices. In other implementations, the server can transfer data to a monitoring device so that a health care professional can view the determined risk indicator and other patient-related data.

As shown in FIG. 3, the server 300 includes components or modules that can be used to compute a risk indicator from a patient's physiologic signal data. Physiologic signal data can be received by the server 300 through an interface 302. In implementations including external devices, the interface 302 may receive data over a communication channel or over a network, for example. In implementations implementing the techniques within implanted devices, the interface may receive sensed signal readings, such as from connected electrodes or other types of sensors (e.g., a pressure sensor). The interface 302 can place the physiologic signal data on a bus 304, which provides interconnectivity between the various modules and components of the server 300. A control module 308 may include hardware and software modules, including one or more processors (not shown) that may execute instructions to perform tasks for the system, such as the steps comprising the methods disclosed herein. Examples of processors that may be suitable can include one or more microcontrollers, microprocessors, central processing units (CPUs), computational cores instantiated within a programmable device or ASIC, and the like. In general, the processor or other control components of the control module 308 may control or manage the flow of information throughout the system, including the flow of information over the bus 304. As is conventional, instructions and data may be stored in a non-volatile data store, and may be moved to a memory 306 for active use. The processor may access the instructions data from memory for execution, for example, and may load the instructions and data into on-chip cache as appropriate.

The control module 308 includes a risk analysis application 310, which can be used to implement the risk analysis techniques discussed herein. The risk analysis application 310 includes a preprocessing sub-module 312, a harmonic sub-module 314, and a risk indicator sub-module 316, each of which may implement portions of the techniques discussed herein. The control module 308 can also optionally include other applications 318a through 318k, which may be used to perform other tasks associated with the device. For example, one of these applications may notify the patient to take specific medications as prescribed by her health care professional at particular times.

The control module 308 may request data from various data stores. For example, a therapy data store 320 may store data relating to patient therapies, a patient data store 322 may store patient-specific information, an application data store 324 may store information relating to graphically displaying cardiac state information, and a physiology data store 326 may store medical information relating to possible cardiac states. The control module 308 can process physiologic signal data and pass the processed data or information derived from analysis of the data to the interface 302 over the bus 304. From there, the interface 302 may forward the data, for example, to a monitoring device.

The server 300 can receive, process, and transmit information regarding periodic variability in a physiologic signal of a patient. The control module 308 can execute instructions that cause the module to receive data and determine periodic variability in a physiologic signal of a patient. For example, the control module 308 can use the risk analysis application 310 to perform harmonic decomposition on a patient's physiologic signal, and determine an estimate of energies associated with certain harmonics of the signal to determine the patient's risk of sudden cardiac death.

In some implementations, the preprocessing sub-module 312 can determine a reference frequency from the physiologic signal data. For example, the preprocessing sub-module 312 can determine a heart rate frequency to use as a reference frequency. In various implementations, the preprocessing sub-module 312 can determine whether baseline noise in the physiologic signal data is below a first predetermined threshold. For example, if the baseline noise exceeds the first predetermined threshold, the risk analysis application 310 can determine that the physiologic data may have too much noise to allow analysis with a desired level of accuracy. Similarly, the preprocessing sub-module 312 can determine if a proportion of ectopic beats or uncorrelated beats exceeds a second predetermined threshold. In some implementations, if the proportion of ectopic beats exceeds the second predetermined threshold, the preprocessing sub-module 312 can determine that an insufficient amount of uncorrupted data remains in the data set. In some implementations, if a sufficiently high proportion of ectopic or uncorrelated beats are identified, an alert indicating a chaotic state may be issued. The pre-processing module 312, or portions of it, can be housed on an implantable device in some implementations to provide initial screening of sensed data prior to storing or transmitting it. This may increase memory and battery usage efficiency within the device. Also, the preprocessing module can be used to remove ectopic or uncorrelated beats so as to avoid contamination of the remaining data and permit better analysis results. In various implementations, the preprocessing sub-module 312 can determine if there is a change in the heart rate that may be considered when analyzing the physiologic signal data. For example, if the server 300 analyzes ECG signal data for T-wave alternans, the server 300 may track the patient's heart rate and adjust risk indicator determinations based on noted changes in the patient's heart rate. Also, for example, filters used in the harmonic decomposition steps may be adjusted as the patient's heart rate changes, and in some implementations only as the patient's heart rate changes, which may result in more efficient harmonic decomposition computation.

Once a reference frequency is established, the harmonic sub-module 314 can be used to implement harmonic decomposition to yield information pertaining to specific harmonics of interest, such as fractional harmonics present in a measured electrical or mechanical physiologic signal. The harmonic sub-module may be used to extract harmonics of the physiologic signal. In some implementations, a hybrid signal may be derived or assembled from the received physiologic signal, and such derivation or assembly may be performed using the preprocessing sub-module 312. For example, in implementations where the received physiologic signal is an ECG signal, a continuous repolarization signal may be assembled by extracting repolarization waves from the ECG signal. Then, harmonics of the continuous repolarization signal may be determined using harmonic decomposition, according to some implementations.

For example, the harmonic sub-module 314 can determine fractional harmonic frequencies. In some implementations, the harmonic sub-module 314 extracts harmonics of the physiologic signal data using filter banks. For example, the harmonic sub-module 314 can use a plurality of filters to determine each harmonic of the physiologic signal data (or of a signal derived from the physiologic signal, such as a continuous repolarization signal). In one implementation, each filter in the filter bank may comprise a filter having a first passband centered at a fractional harmonic frequency of interest and a second passband centered at an integer harmonic frequency of interest. When fed the input signal, each of the filters in the bank can then pass an integer-fractional harmonic frequency pair, and the resultant pairs can be added to form a blended signal that includes an integer-fractional harmonic pair of interest. Such integer-fractional harmonic pairs of interest can include one or more of a 0.5 HR and 1 HR pair (that is, a pair including the fractional harmonic corresponding to a frequency of 0.5 times the reference frequency, and the first integer harmonic), a 1.5 HR and 2 HR pair (that is, a pair including the fractional harmonic corresponding to a frequency of 1.5 times the reference frequency, and the second integer harmonic), a 2.5 HR and 3 HR pair (that is, a pair including the fractional harmonic corresponding to a frequency of 2.5 times the reference frequency, and the third integer harmonic), and so on.

Following extraction of the integer-fractional harmonic pairs of interest (e.g., one pair, two pairs, three pairs, four pairs, five pairs, etc.), the harmonic sub-module 314 may add the extracted pairs to form a blended signal comprising a summation an extracted fractional harmonic—integer harmonic pair. Using a blended signal may allow a step of separating the energies of fractional and integer harmonics to be postponed until a later stage, when a shorter filter can be used, according to some implementations. The harmonic sub-module 314 may then apply band-pass filters to the complex envelope of the blended signal to extract the fractional harmonics, which can then be used to determine a TWA amplitude for the patient, as will be further described below. The disclosure, however, contemplates extracting the fractional harmonics directly from the input signal (e.g., either the received physiologic signal or a signal derived from the received signal, such as a continuous repolarization signal).

In some implementations, the harmonic sub-module 314 can use sub-band coding to compress and clean the harmonic signals. For example, the harmonic sub-module 314 can find fiducial points, or peaks and valleys, of the harmonics. Tracking of successive order fiducial points can be used to determine if there are phase anomalies, such that they may be removed. Similarly, in the harmonic sub-module 314, interpolation over the fiducial points can be used as an estimate of a signal envelope.

Using harmonics from the physiologic signal data (or e.g., the repolarization signal data), the risk indicator sub-module 316 can compute an alternans power by finding each harmonic's amplitude. For example, the risk indicator sub-module 316 can demodulate the signal envelope to separate fractional harmonics and a noise band with band-pass filters. The risk power, or TWA power in implementations concerned with calculating TWA amplitudes, can be computed as a sum of products of the fractional harmonics and their corresponding conjugates. In some implementations, the computed risk power is adjusted by a power estimate of the noise band. In other implementations, the risk power can be estimated directly from the demodulated signal envelope. In some implementations, the risk power can be normalized by a power of the physiologic signal computed as a sum of products of integer harmonics and their corresponding conjugates to ensure measurement robustness to changes in the physiologic signal data. The risk indicator is calculated as a square root of the risk power, which may be adjusted for effects of noise or physiologic signal power in some implementations.

The control module 308 can determine information to transmit regarding periodic variability in a physiologic signal of a patient. For example, the control module 308 can reconstruct a T-wave alternans signal from the T-wave's fractional harmonics. In some implementations, other applications 318a through 318k can compile a display of the reconstructed T-wave alternans signal. In other implementations, the control module 308 can receive information from other sources and apply the information to calculations in the risk analysis module. In some implementations, an onset heart rate at which TWA become significant and sustained may be used in determining a risk profile for the patient.

Information applied to calculations determined in the risk analysis application 310 can include data from various data stores within the server 300. Example data stores can include the therapy data store 320, the patient data store 322, the application data store 324, and the physiology data store 326. These data stores can store received information from a health care professional. The data stores can also store information received from a patient. The data stores can be updated on a periodic basis. In the depicted implementation, the data stores 320-326 reside within the server 300, but in other implementations one or ore of the data stores 320-326, or other data stores storing other relevant information, may be external to the device, and may be accessed by the device or by another device that provides the information to the server 300.

The therapy data store 320 can store information regarding patient therapy methods, such a drug pump, electro acupuncture therapy to induce parasympathetic activation, a cardiac rhythm management device, or oral medications. For example, this information can provide data to the control module 308 to determine heart rate thresholds or risk indicator thresholds.

Information regarding the patient can also aid in determining patient cardiac state. The patient data store 322 can include patient information such as drug allergies, previous cardiac history, and current or historical health care providers. The control module 308 can use information from the patient data store to modify an assessment of the patient's cardiac state.

The physiology data store 326 can also provide information to aid in determining cardiac state by including the patient's physical data. The physiology data store 326 can include patient vital signs from previous visits, other risk markers determined with external or implantable devices, such as a burden of non-sustained ventricular tachycardia, and other pre-existing conditions, to list just a few examples. This data can be used with the techniques described here to provide a more accurate risk assessment, according to some implementations.

Figure 4:
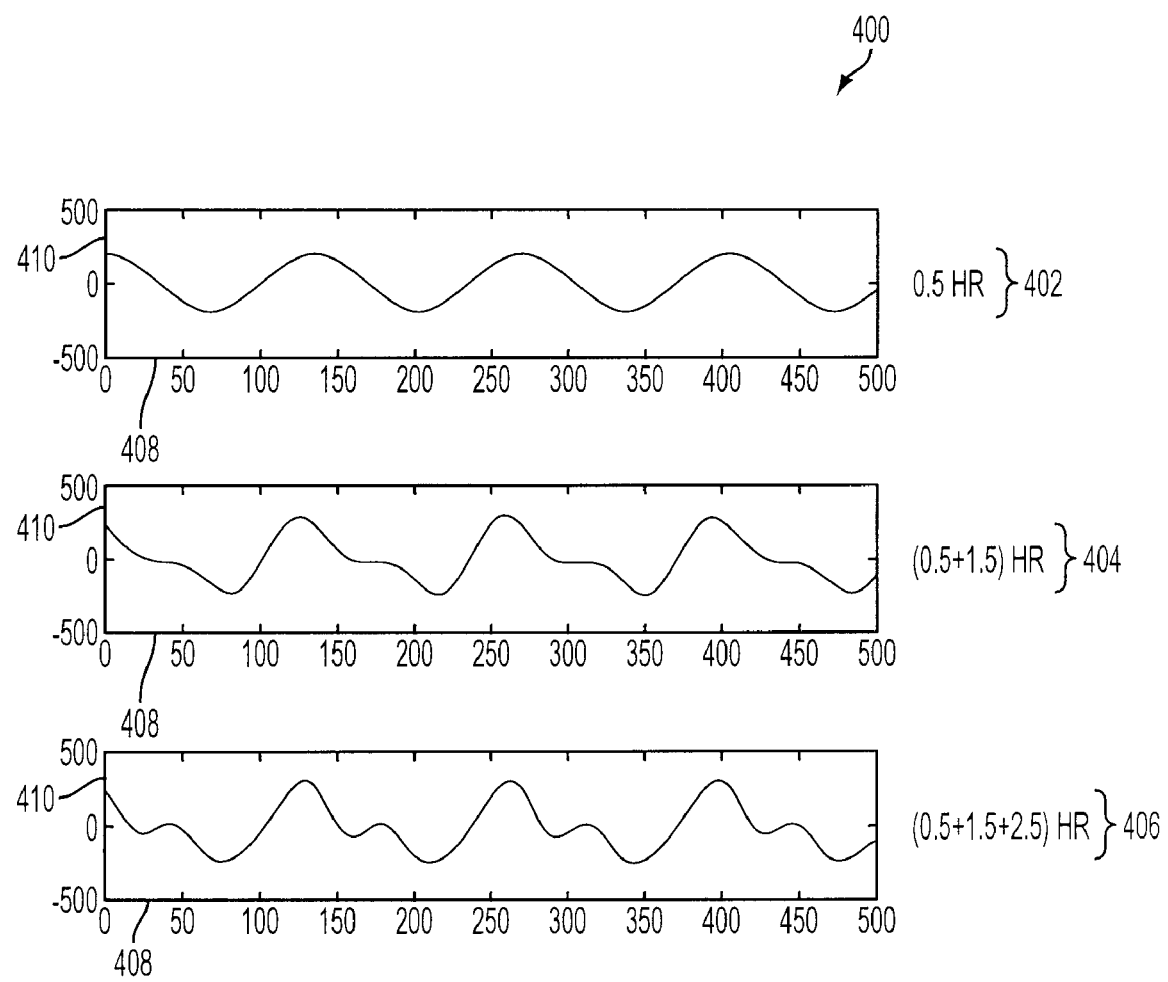
FIG. 4 is an exemplary collection of graphical representations of alternans signal reconstruction from fractional harmonics.

FIG. 4 is an exemplary collection of graphical representations of alternans signal reconstruction from fractional harmonics. In general, a physiologic signal can be analyzed through fractional harmonics, or frequencies that are multiples of one half of the heart rate. Amplitudes of the fractional harmonics can be determined, and can be used in an assessment of periodic variability in a physiologic signal of a patient, such as whether or not the patient may be experiencing the onset of ventricular tachycardia.

An integer harmonic of a wave is a signal that corresponds to an integer multiple of the fundamental frequency. A fractional harmonic of a wave is a signal that corresponds to a fractional or non-integer multiple of the fundamental frequency. The discussion herein focuses on fractional harmonics that are multiples of one half of the fundamental frequency (that is, frequencies of 0.5×, 1.5×, 2.5×, etc., fundamental frequency). A first fractional harmonic 402 is shown as 0.5 of a heart rate. This harmonic can correspond to alternating (or every other) beats in the physiologic signal. A first and second harmonic 404 is shown as 0.5+1.5 of the heart rate. These harmonics can correspond to every third beat in the physiologic signal. First, second, and third harmonics 406 are shown as 0.5+1.5+2.5 of the heart rate. These harmonics can correspond to every fifth beat in the signal. The FIG. 4 graphs 402-406 include a time axis 408 and an amplitude axis 410.

Figure 5:
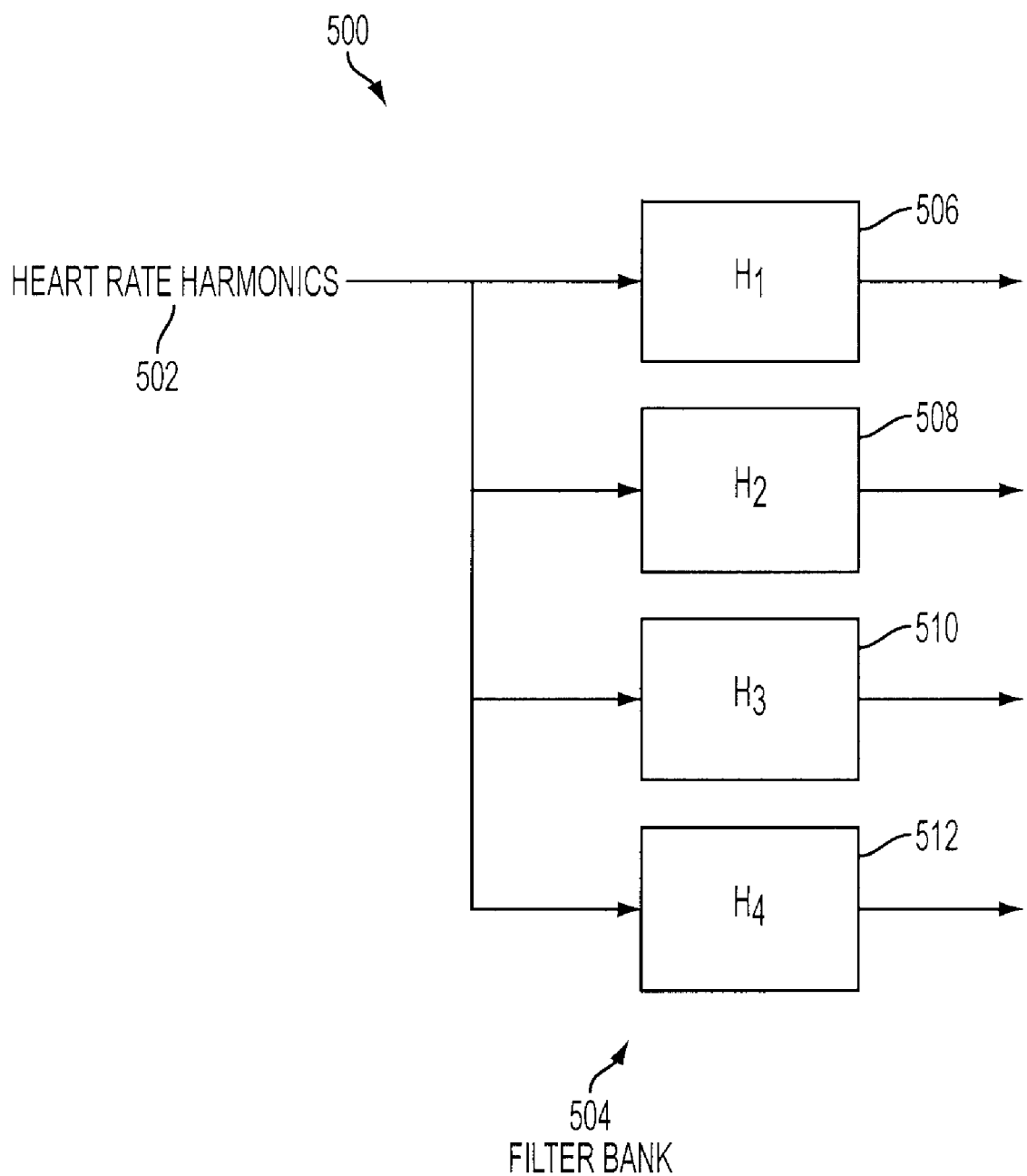
FIG. 5 is a block diagram of an example filter bank that can be used to process a physiologic waveform.

FIG. 5 is a block diagram 500 of an example filter bank that can be used to process a physiologic waveform. In general, a physiologic signal can be decomposed into harmonics using a plurality of filters, such as a plurality of band-pass filters, according to an implementation. Generally, band-pass filters pass a band of frequencies within a so-called passband, and attenuate frequencies outside (higher or lower) of the passband.

In an implementation, a signal 502, such as a repolarization signal, can be sent through a filter bank 504 to determine specific harmonics of interest. A first filter 506 can correspond to a first harmonic or harmonics of interest, a second filter 508 can correspond to a second harmonic or harmonics of interest, a third filter 510 can correspond to a third harmonic or harmonics of interest, and a fourth filter 512 can correspond to a fourth harmonic or harmonics of interest. In some implementations, each of the filters 506-512 may include two passbands, one centered at the fractional harmonic of interest and the second centered at an adjacent integer harmonic of interest. For example, the first filter 506 may be used extract the fractional harmonic associated with a frequency of 0.5 times the reference frequency and the integer harmonic associated with the fundamental frequency. Similarly, the second filter 508 may be used to extract the 1.5 fractional and 2 integer harmonics; the third filter 510 may be used to extract the 2.5 and 3 harmonics; and the fourth filter may be used to extract the 3.5 and 4 harmonics. Alternative filter banks are contemplated, such as a filter that includes only the first filter 506, a filter bank that includes the first and second filters 506, 508, or a filter bank that includes the first three filter banks 506, 508, 510. Similarly, the heart rate history can be tracked and the filter bank 504 can be adjusted to capture the harmonic frequencies only where heart rate has changed.

Other implementations may use a filter bank with filters that target only the fractional harmonics for extraction. However, because energy from integer harmonics may encroach on the fractional harmonics, narrow filters may be used to sufficiently isolate the fractional harmonics, such that energy from the integer harmonics does not corrupt later computations. Using a filter bank targeting only the fractional harmonics for extraction may also require longer sets of physiologic data acquired while the heart rate conforms to certain heart rate limits to provide the same level of accuracy.

Figure 6:
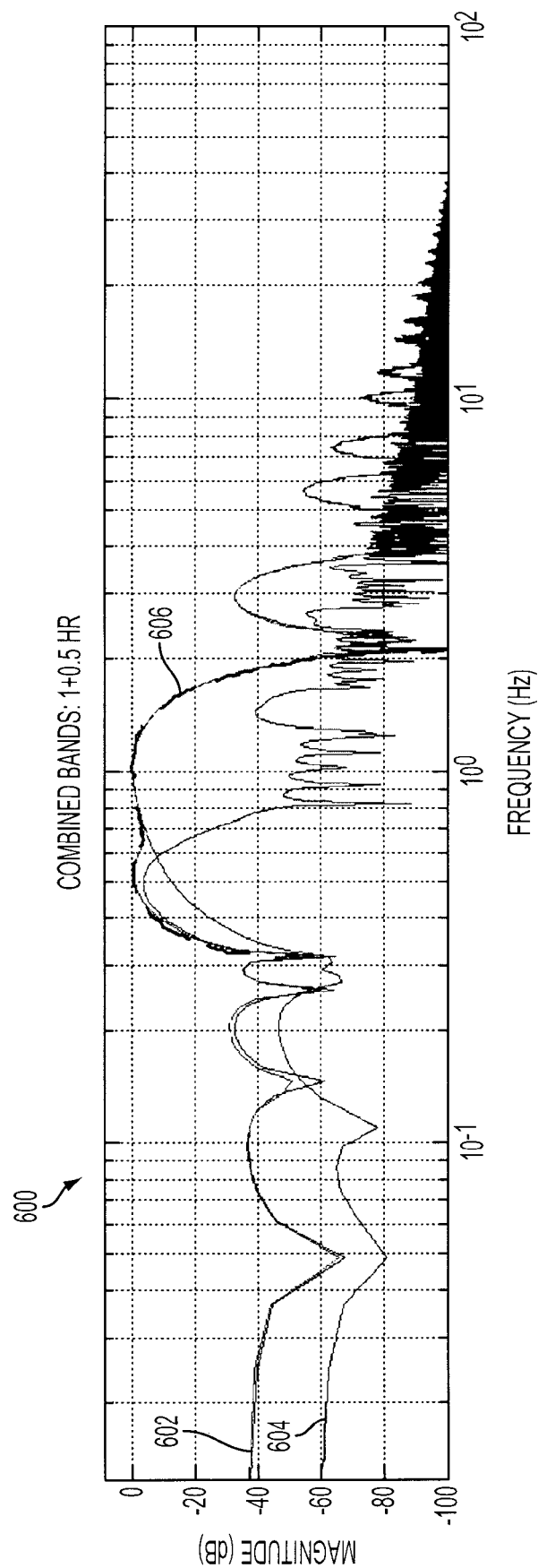
FIG. 6 is a graphical display 600 of an exemplary dual-passband filter with bandpasses centered at a first integer harmonic and a first fractional harmonic.

FIG. 6 is a graphical display 600 of an exemplary dual-passband filter 606 with bandpasses centered at a first integer harmonic and a first fractional harmonic. In general, a dual-passband filter can be used to isolate a harmonic pair, such as in integer-fractional harmonic pair. The filter 606 may correspond to one of the filters 506-512 implemented in the filter bank 504 of FIG. 5 and discussed above, for example. The pairs of harmonics can be later separated to determine further information. Fractional harmonic 602 and integer harmonic 604 of physiologic signal data are shown with a band-pass filter 606 having passbands centered around the first fractional harmonic and the first integer harmonic. In some implementations, separate band-pass filters can be included for each pair of fractional and integer harmonics of interest. For example, an implementation may include a first band-pass filter for the first fractional harmonic and a second band-pass filter for the first integer harmonic. For each band-pass filter, the cutoff frequencies can be selected to avoid or minimize picking up energies of the next pair of harmonics.

Figure 7:
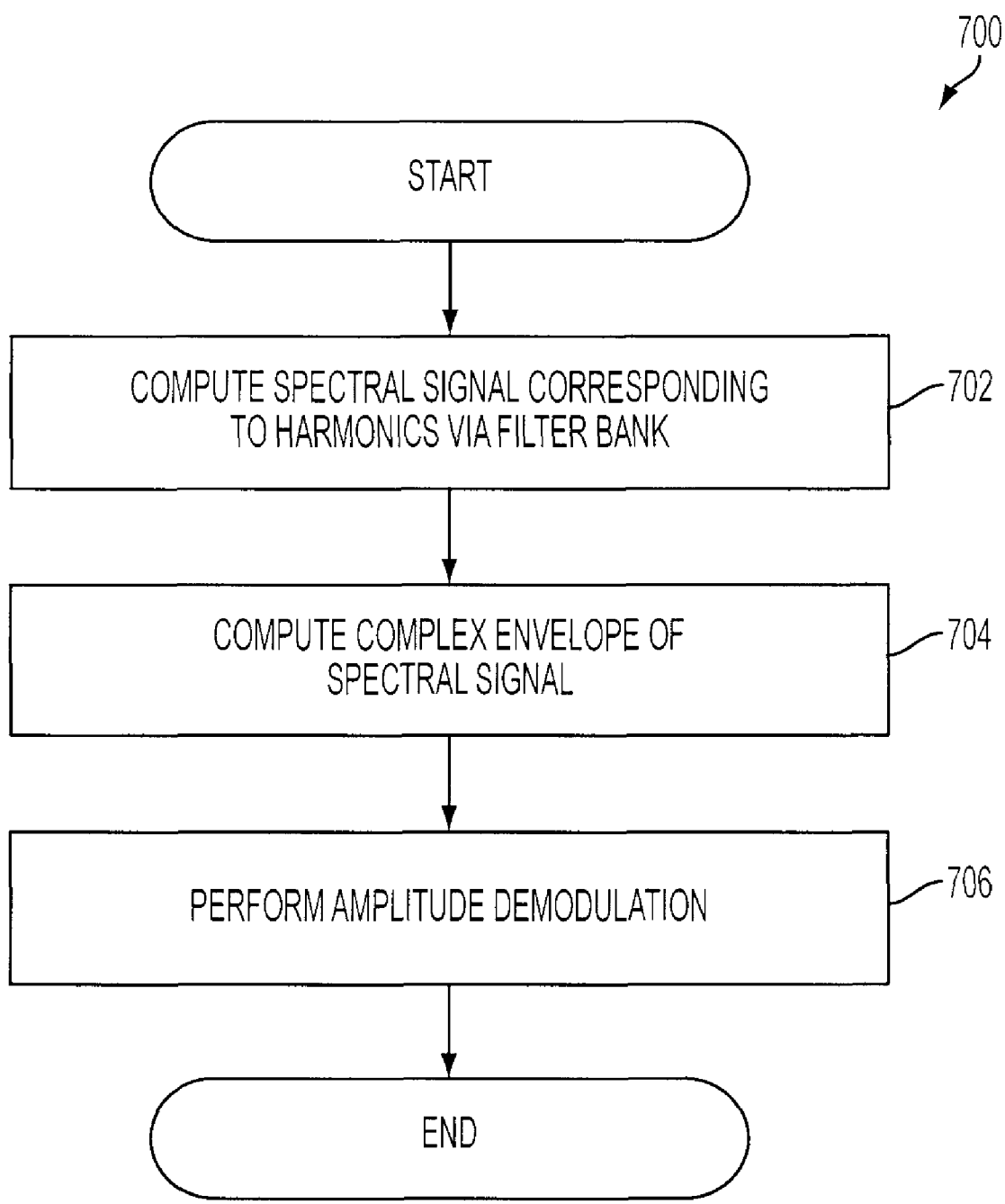
FIG. 7 is a flow chart of exemplary operations that can be executed to perform harmonic decomposition.

FIG. 7 is a flow chart 700 of exemplary operations that can be executed to perform harmonic decomposition. The process 700 generally involves computing a spectral signal corresponding to harmonics via a filter bank, computing a complex envelope of a blended harmonic signal, and performing amplitude demodulation on the complex envelope signal.

At an initial step 702, a spectral signal corresponding to heart rate harmonics is computed via a filter bank. In some implementations, the filter bank can contain band-pass filters to separate the heart rate harmonics. For example, each band-pass filter can separate harmonics into pairs, such as a first fractional harmonic with a first integer harmonic.

Next, a complex envelope of the spectral signal may be computed (704). The harmonic signal can be sampled at fiducial points. Fiducial points in the harmonic signal are peaks and valleys. In some implementations, the sequence of peaks and valleys is tracked to detect and remove phase anomalies. In some implementations, the complex envelope can be computed by interpolating over peaks for maximum amplitude and valleys for minimum amplitude.

Next, at step 706, amplitude demodulation can be performed on the complex envelope of the harmonic signal. For example, a fractional harmonic and a noise band can be separated from the complex envelope. A bandpass filter can be used to extract an amplitude corresponding to a fractional harmonic. In some implementations, the risk power is computed by aggregating products of the fractional harmonics and their conjugates. In some implementations, the risk power can be estimated directly from the demodulated complex envelope. In other implementations, the power of the noise band can be estimated and used to adjust the alternans power. In still other implementations, the alternans power be normalized by T-wave power computed as the sum of products of the integer harmonics and corresponding conjugates.

Figure 8:
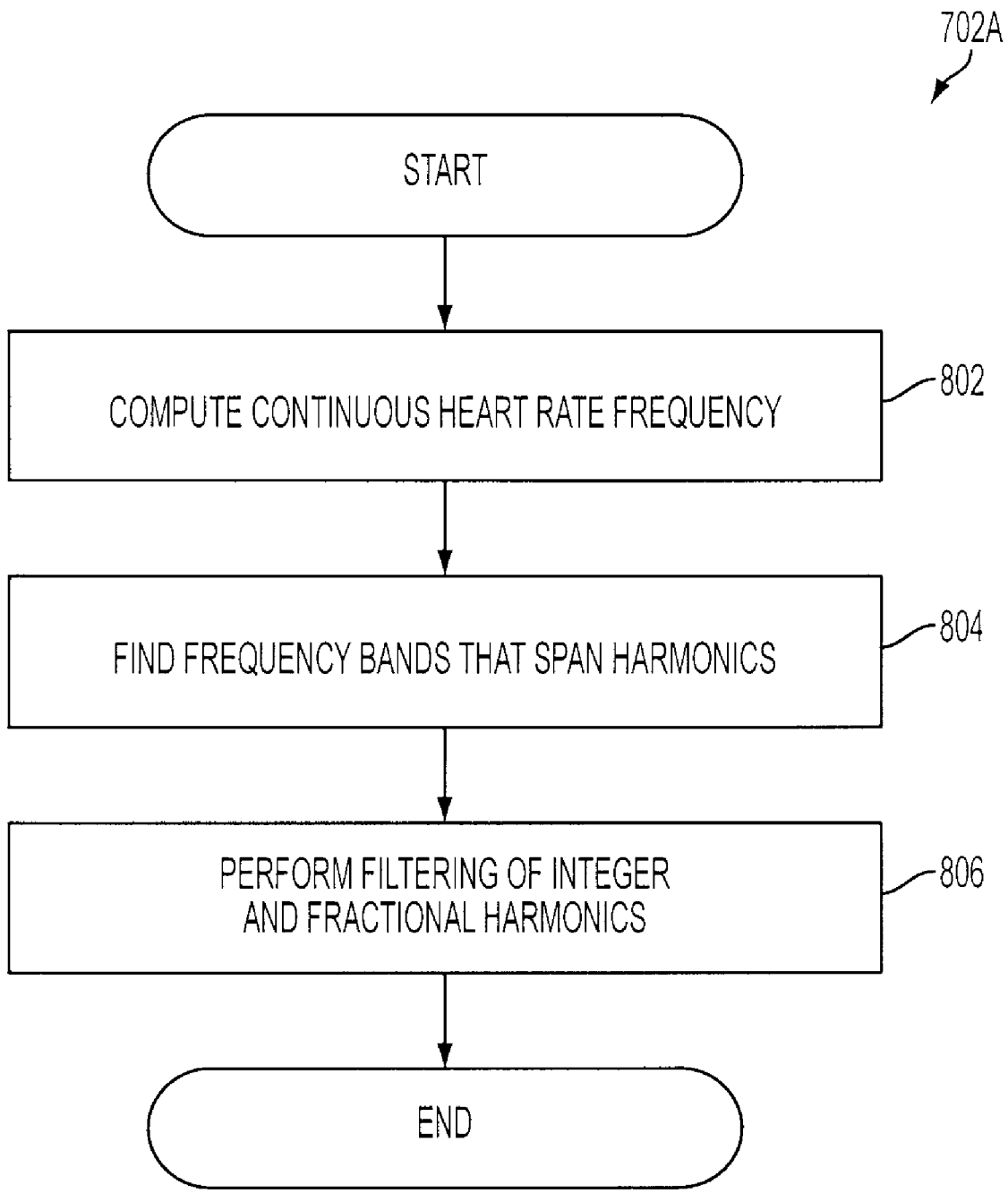
FIG. 8 is a flow chart of exemplary operations that can be executed to compute a spectral signal corresponding to harmonics.

FIG. 8 is a flow chart 702A of exemplary operations that can be executed to compute a spectral signal corresponding to harmonics. In some implementations, the flow chart 702A may correspond to step 702 of flow chart 700 in FIG. 7, described above. The process 702A generally involves computing a continuous heart rate frequency, finding frequency bands that span harmonics, and performing filtering of integer and fractional harmonics.

At an initial step 802, a continuous heart rate frequency is computed. The heart rate frequency may be used as a central or fundamental frequency of the physiologic signal for harmonic decomposition. In some implementations, the central frequency can determine other harmonics within the physiologic signal data (or a signal derived from the physiologic signal, such as a repolarization signal).

Next, frequency bands are found that span harmonics of the central frequency (804). For example, filters having characteristics of a combination of first and second band-pass filters can be used. In some implementations, the first band-pass filter in the combination can be chosen to identify a fractional harmonic, and the second band-pass filter in the combination can be chosen to identify an integer harmonic. In another implementation, the filter can include two passbands, one to pass the fractional harmonic and the other to pass the integer harmonic of the input signal.

Next, at step 806, filtering of integer and fractional harmonics is performed. In some implementations, harmonic pairs can be determined iteratively. For example, the first harmonic pair can be determined, then the second harmonic pair can be determined, then the third harmonic pair, and next the fourth harmonic pair can be determined. In various implementations, a phase-lock loop can be used to determine harmonic pairs within the physiologic data. In other implementations, a filter bank can be used to determine the integer-fractional harmonic pairs. For example, a first band-pass filter in a combination can be chosen to identify a fractional harmonic, and a second band-pass filter in the combination can be chosen to identify an integer harmonic. In this example, the first integer harmonic and the first fractional harmonic can be extracted with one filter, which can be a convolution of the two filters including both pass bands.

Figure 9:
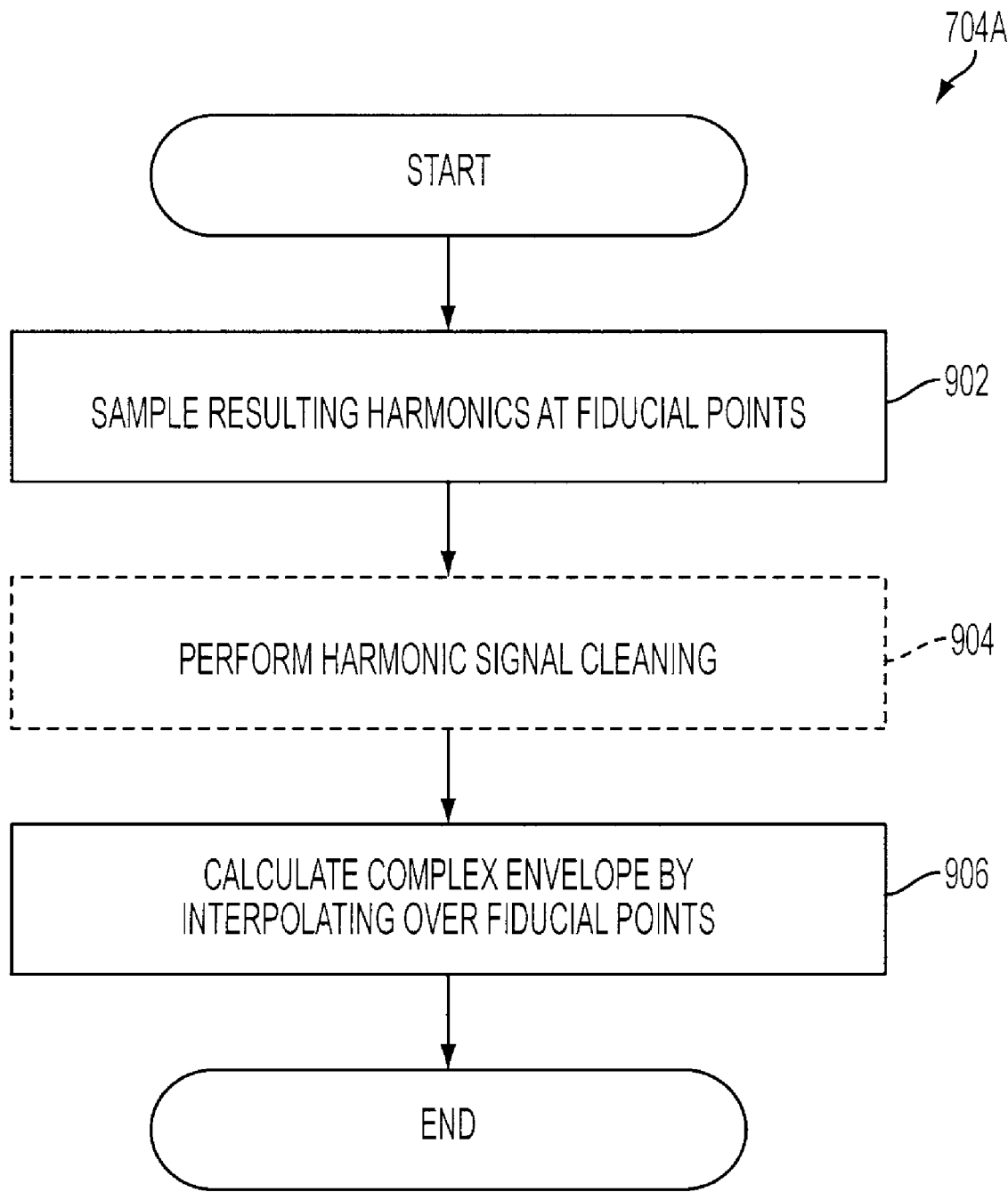
FIG. 9 is a flow chart of exemplary operations that can be executed to calculate a complex envelope of modulated harmonics.

FIG. 9 is a flow chart showing a exemplary operations 704A that can be used to implement step 704 of the FIG. 7 flowchart. The process 704A generally involves sampling resulting harmonics at fiducial points, optionally performing harmonic signal cleaning, and calculating a complex envelope via interpolation over fiducial points. In some implementations, the process 704A can correspond to the step (704) in FIG. 7 where the complex envelope of the spectral signal is computed, discussed above.

At an initial step 902, resulting harmonics are sampled at fiducial points. The resulting harmonics may be, for example, harmonics comprising the spectral signal generated at step 702 in the flow chart 700 of FIG. 7, according to some implementations. As described above, fiducial points can also be described as peaks and valleys of the harmonics, or points of the harmonic where the slope of the harmonic changes sign. In some implementations, fiducial points can be used to detect phase anomalies and remove them.

Next, at box 906, a complex envelope is calculated by interpolating over the fiducial points of the harmonics. In some implementations, interpolation over the fiducial points can be used as an estimate of a complex envelope that spans or encompasses the harmonics. For example, the complex envelope can be computed by interpolating over peaks for maximum amplitude and valleys for minimum amplitude.

Figure 10:
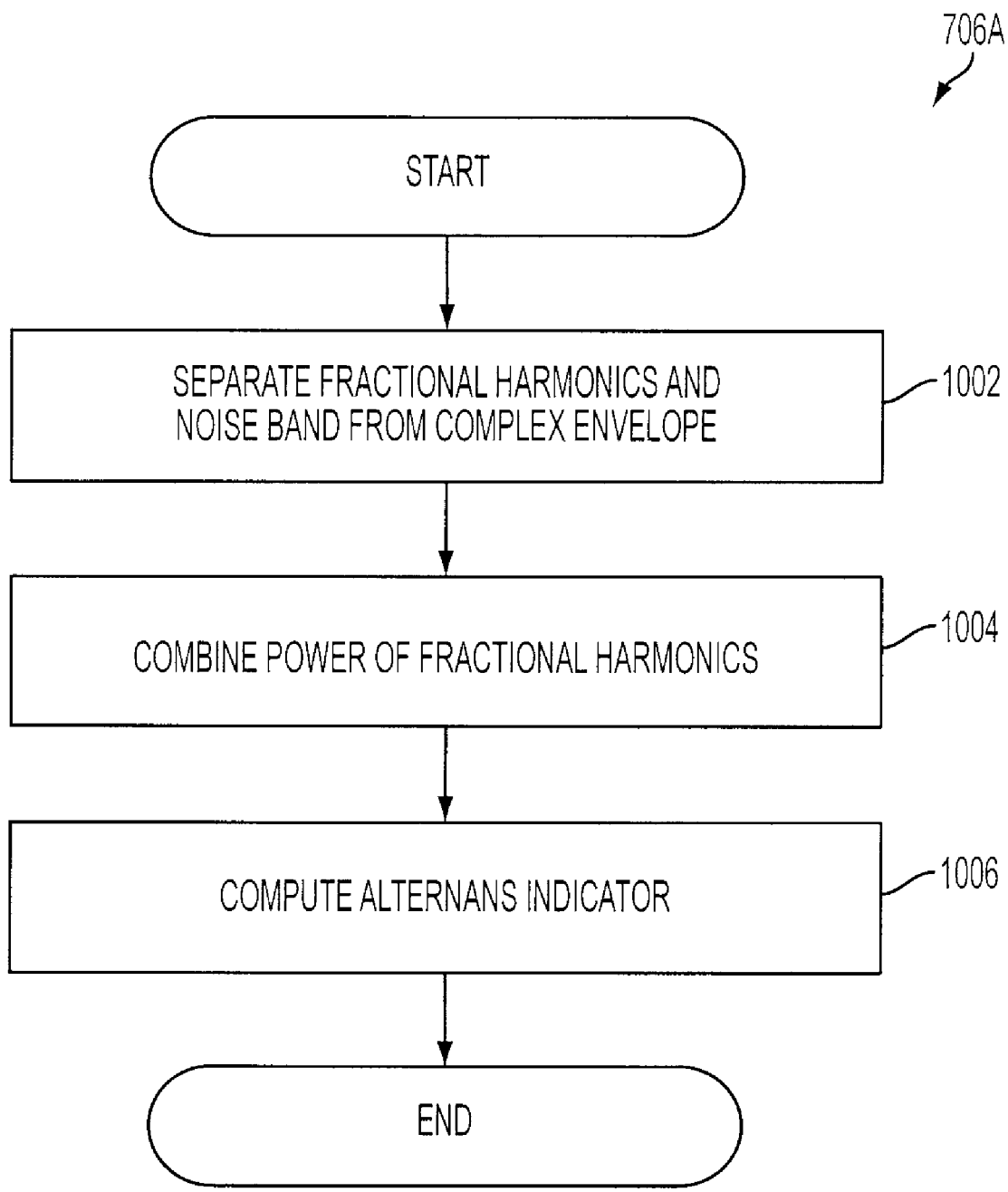
FIG. 10 is a flow chart of exemplary operations that can be executed to extract an alternans power from a complex envelope.

FIG. 10 is a flow chart 706A of exemplary operations that can be executed to extract an alternans power from a complex envelope. The process 706A generally involves separating fractional harmonics and a noise band from a complex envelope, combining powers of fractional harmonics, and computing a risk indicator. The process 706A can correspond to the step 706 of the flow chart 700 in FIG. 7, described above.

At an initial step 1002, fractional harmonics and a noise band are separated from a complex envelope. The complex envelope may correspond to the envelope calculated in step 906 of the flow chart 704A of FIG. 9, according to some implementations. In some implementations, the noise band can be separated from the complex envelope using a linear-phase band-pass filter. The linear-phase band-pass filter can be used to determine baseline noise from the signal, as will be further described below.

Next, the powers of the fractional harmonics can be combined (1004). For example, a product of a fractional harmonic and its corresponding conjugate can determine the power of the harmonic. In some implementations, the powers of the fractional harmonics are computed as an alternans power. The alternans power is computed as a sum of products of the fractional harmonics and their corresponding conjugates. In other implementations, the power of the fractional harmonics can be estimated directly from the demodulated complex envelope.

Next, at step 1006, an alternans indicator can be computed. For example, the risk indicator can be calculated as a square root of the risk power determined in step 1004. In some implementations, the alternans power may be adjusted for effects of noise or physiologic signal power. In some implementations, the risk indicator can represent a T-wave alternans amplitude determination. The risk indicator may be used by a physician or the device to assess a risk of sudden cardiac death or other cardiac conditions. In some implementations, determination of the risk indicator or alternans indicator includes consideration of underlying factors such as an onset heart rate for the alternans.

As described above, in some implementations, a noise band can be separated from the complex envelope. In some implementations, the computed alternans power is adjusted by a power estimate of the noise band. In some implementations, the alternans power can be normalized by a power of the physiologic signal computed as a sum of products of integer harmonics and their corresponding conjugates to ensure measurement robustness to changes in the physiologic signal data.

Some implementations of the techniques described above may allow reconstruction of alternans signal morphology (e.g., TWA morphology), as harmonic components of the input signal or a signal derived from the input signal can be isolated and analyzed to determine an alternans indicator that preserves important risk information from the signal. The morphology of TWA might be correlated to instability origin, ion imbalance, or ischemia location. Also, some implementations of the disclosed techniques may provide improved robustness, as data loss that can be caused by premature ventricular contractions (PVCS) or atrial fibrillation, may be minimized. Improved T-wave alternans amplitude computation may be achieved using some implementations of the techniques, devices, and systems described here, as T-wave alternans amplitude may be considered independent of the amplitude of the repolarization wave. Some implementations of the time-frequency analysis techniques disclosed herein may also be implemented in a computationally efficient manner, as full spectral analysis may be replaced by analysis of specific harmonics of the signal of interest. This may enable the techniques to be implemented on devices that operate on battery power, and which may be sensitive to power consumption, such as some implantable monitoring devices or implantable medical devices.

Figure 11:
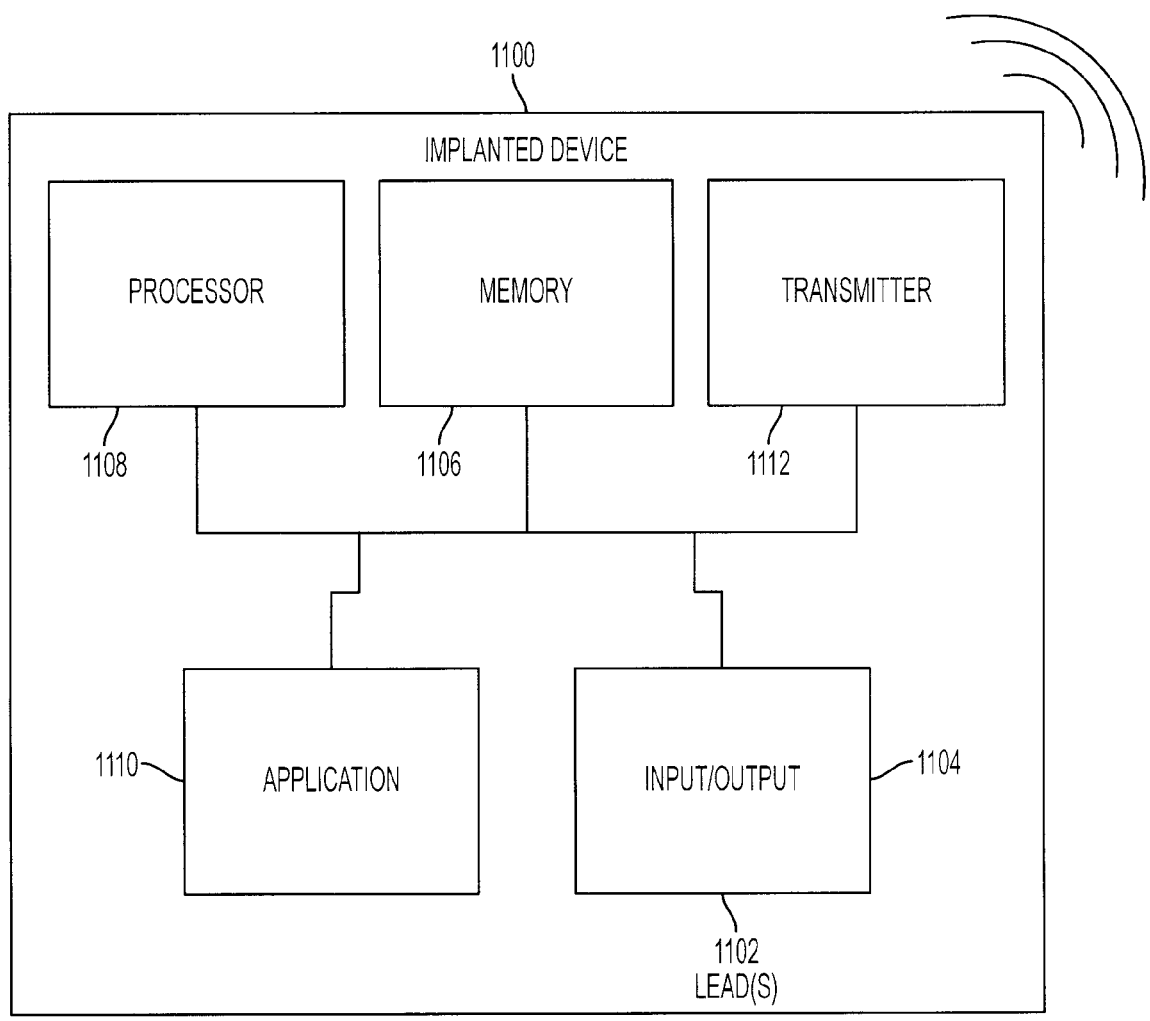
FIG. 11 is a block diagram of an exemplary telemetry system including an implanted device that can be used to accurately measure periodic variability in a physiologic signal of a patient.

FIG. 11 is a block diagram of an exemplary implantable device 1100. In some implementations, the device 1100 can implement any of the methods described herein. While not shown here for simplicity, in general the device 1100 may include some or all of the components discussed above with reference to the device 300 of FIG. 3, including the risk analysis application 310 and its associated sub-modules. In other implementations, the device 1100 can implement a portion of some of the methods described herein (e.g., the device may sense a physiologic signal, store the signal, and wirelessly transmit the signal or a portion of the signal to an external device for further processing). Implementations of the device 1100 can be used to accurately measure periodic variability in a physiologic signal of a patient. In general, the implanted device 1100 records and processes to a patient's physiologic signal data, according to some implementations. For example, the implanted device 1100 can record ECG signal data to determine whether or not the patient has a risk of sudden cardiac death by calculating her T-wave alternans amplitude. In other examples, the device 1100 may record a mechanical signal, such as a mechanical pulsus signal associated with a patient's blood pressure. In some implementations, the device may sense and record multiple physiologic signals, such as both an electrical signal and a mechanical signal, either or both of which may be analyzed (independently or cooperatively) to determine an alternans indicator of a cardiac event or condition. In some implementations, the computed alternans indicator can be combined with one or more other risk markers, which may provide an enhanced patient risk profile.

The depicted device 1100 includes one or more leads 1102, which may be configured for positioning inside or outside of a patient's heart or other bodily organ, depending on the implementation, an input/output module 1104, a memory 1106, a processor 1108, an application module 1110, and a transmitter 1112. In some implementations, the implanted device 1100 can incorporate the transmitter 1112 and the input/output module 1104 into the same module. Other implementations are discussed further below.

The one or more leads 1102 can include one or more electrodes that can sense signal data, including physiologic signal data of the patient. In some implementations, the one or more leads 1102 are intracardiac leads; in some implementations, the one or more leads are configured for subcutaneous location within a patient; in some implementations, at least one intracardiac and at least one subcutaneous lead are included. In some implementations, the one or more leads 1102 may be replaced or supplemented with one or more sensors or ports configured to sense a mechanical signal. Some implementations may include one or more catheters that may facilitate mechanical measurements at a distance from the device.

In some implementations, the processor 1108 can use the physiologic signal data to determine a heart rate of the patient. For example, the processor 1108 can analyze the physiologic signal data to determine the heart rate, and can use this determination in calculating a cardiac state of the patient, including deciding whether or not to make an assessment in various situations. For example, in some implementations, ECG data may be stored for TWA analysis only during periods where the heart rate is elevated, or during periods where the heart rate is elevated and stable for a predetermined period. In another example, the processor 1108 can track an onset heart rate at which TWA become significant and sustained to verify the determination of the cardiac state of the patient. The processor can measure baseline noise in the physiologic signal and reject storing the signal segment if the noise exceeds a predetermined threshold.

The processor 1108 can calculate an alternans indicator using harmonic decomposition to isolate harmonics of interest to be used in the indicator calculation. Electrical or mechanical signals may be analyzed. In some implementations, the processor 1108 can use a mechanical pulsus signal to determine risk of sudden cardiac death through determining the heart rate, calculating multiple harmonics of the mechanical pulsus signal data, computing power for the harmonics, and determining the alternans indicator. In other implementations, the processor 1108 can use an ECG signal to determine risk of sudden cardiac death by determining the heart rate, calculating multiple heart rate harmonics of the QRS waveform of the ECG signal, computing power for the harmonics, and determining the risk. In still other implementations, the processor 1108 can use an ECG signal to determine risk of sudden cardiac death through determining the heart rate, calculating multiple heart rate harmonics of the repolarization waveform of the ECG signal, computing power for the harmonics, and determining an amplitude for the T-wave alternans.

Figure 12:
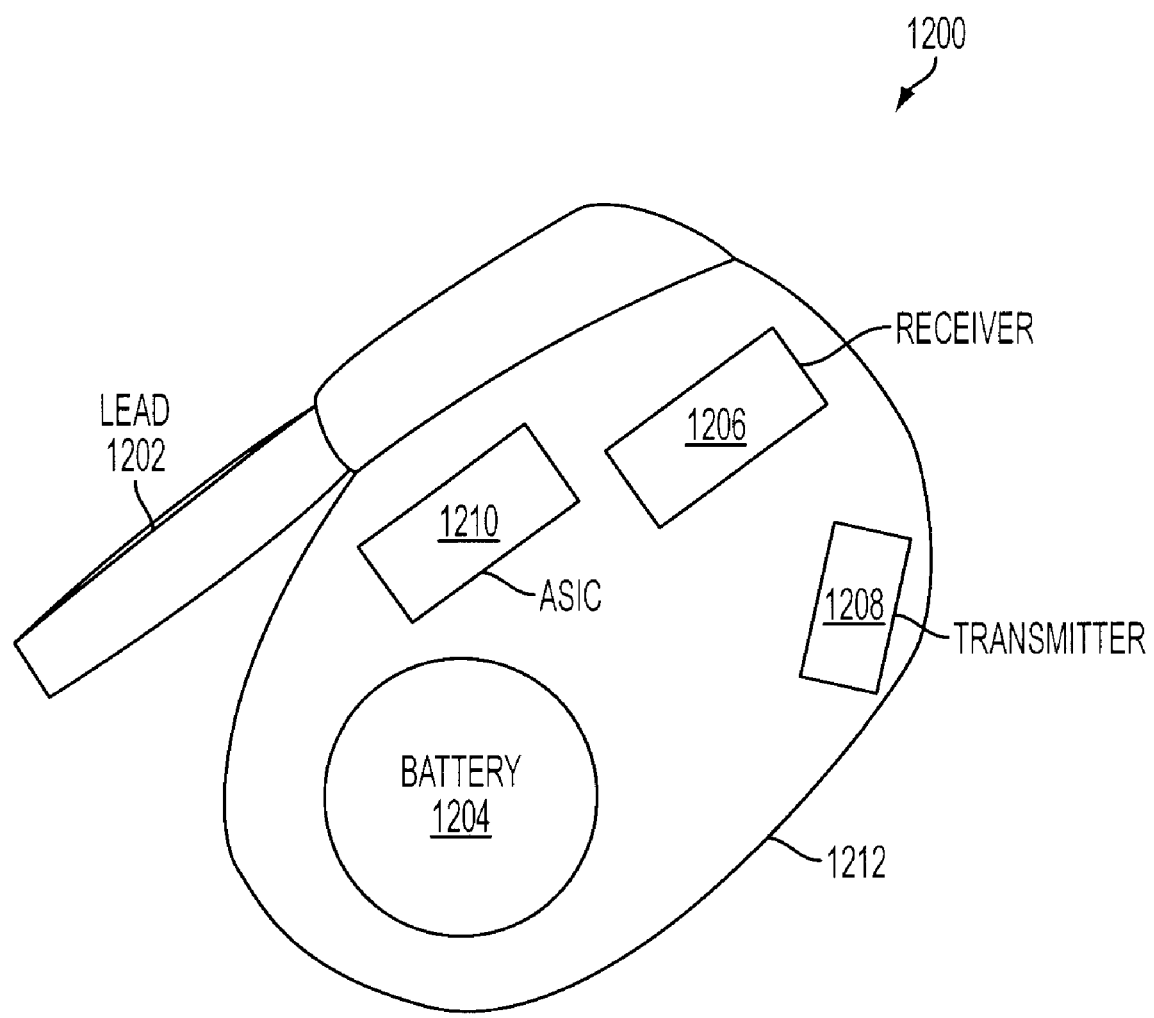
FIG. 12 is a drawing of an exemplary implantable device that can be used to estimate periodic variability in a physiologic signal.
Figure 13:
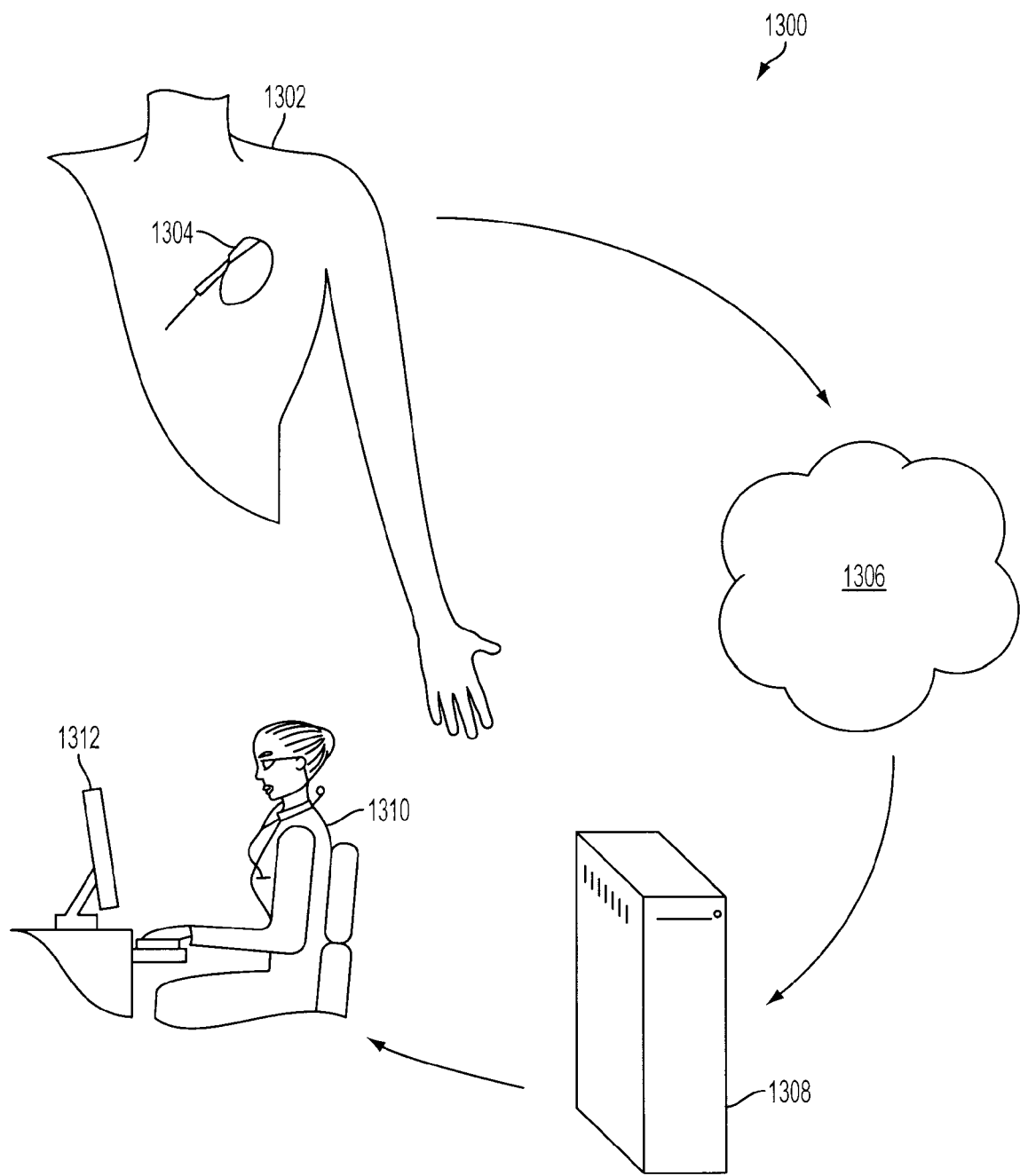
FIG. 13 is an exemplary system that includes a sensing device and external equipment that can be used to estimate periodic variability in a physiologic signal of a patient.

FIGS. 12-13 show exemplary implementations of devices and systems that can be used to implement the techniques described herein. Many variations are possible. For example, external sense electrodes or sensors may be used to sense a physiologic signal. In implementations that utilize an implanted device, the electrodes or sensor(s) may be located in any appropriate monitoring location, including within an organ of the body (e.g., heart), within an artery or vein, or subcutaneously positioned, to list just a few examples.

FIG. 12 is a block diagram of an exemplary implantable device 1200 that can be used to estimate periodic variability in a physiologic signal. In general, the implanted device 1200 senses data relating to a patient's cardiac state and transmits it to an external device for analysis, which may facilitate dynamic monitoring of the patient's cardiac health. Some implementations of the device 1200 analyze the measured signal using the techniques disclosed herein, and results of the analysis may be transmitted from the device to an external device. For example, if a patient has a known cardiac condition, the device can be implanted to provide dynamic monitoring of one or more physiologic signals that contain cardiac information, which signals can be analyzed to determine an alternans indicator that can be used to prevent further serious cardiac events.

Referring to the exemplary implementation shown in FIG. 12, an implanted device 1200 includes a lead 1202, a battery 1204, a receiver 1206, a transmitter 1208, and an application specific integrated circuit (ASIC) 1210 contained within a housing 1212. In some implementations, the implanted device also includes a separate processor, though in this implementation the processor or control unit may be contained within the ASIC 1210. The processor can analyze data collected from the patient to be transmitted to an external device later. Other implementations are discussed further below.

In some implementations, the receiver 1206 can be configured to receive command signals. For example, the receiver 1206 can receive a command that indicates a segment of the physiologic signal data should be recorded and transmitted. In other implementations, the receiver 1206 can receive a command signal indicating that the implanted device 1200 should record and transmit a segment of the physiologic signal data on a specified periodic basis, such as hourly, daily, or weekly. In other implementations, the receiver 1206 can receive a command signal indicating that the implanted device 1200 can record and transmit a segment of the physiologic signal data based on a derived trigger parameter. For example, if the implanted device 1200 is measuring ECG signal data to determine T-wave alternans amplitude, the trigger parameter can be a sustained elevation in the patient's heart rate.

Once the receiver 1206 receives a command signal to activate recording, the receiver 1206 can be configured to transmit an activation signal to the ASIC 1210. In some implementations, the ASIC is a static random access memory (SRAM) device. The ASIC 1210 can store segments of the physiologic signal data, according to some implementations. For example, the ASIC 1210 can record physiologic signal segments based on a predetermined number of heartbeats or time interval. In some implementations, the segments can contain 128 heartbeats. In other implementations, the ECG signal data segments can contain 256 heartbeats, or any other appropriate number of beats. In some implementations, the implanted device 1200 can use determinations from the physiologic signal data to decide whether to continue recording. In some implementations, the ASIC 1210 includes embedded memory for storing collected data or processed data. Additional memory (not shown) may be provided and the ASIC 1210 (or a processor, e.g.) may access the memory as necessary. In some implementations, the implanted device 1200 may not include an ASIC 1210.

The device 1200 collects physiologic data using sensing electrodes. Various combinations of leads and electrodes are possible. As one example, the device may include a single lead 1202 with a single electrode, and may include a second electrode on the housing 1212. In another implementation, there may be no leads connected to the housing 1212. Alternatively, the lead 1202 may include multiple electrodes. In some cases, more than one lead can be used. Leads can be implanted outside the heart, the device 1200 can have intercardiac leads, or leads can be placed both inside and outside the heart.

Following capture of the sensed data, the data can be provided to the transmitter 1208. The transmitter 1208 can send the ECG signal data to an external device, such as a server 300 (FIG. 3), or to a monitoring device. In some implementations, the implantable device 1200 may directly wirelessly transmit data to an intermediate external device, such as a base station, which may then transmit the data over a network to the server.

FIG. 13 is an exemplary system 1300 that includes a sensing device 1304 and external equipment that can be used to estimate periodic variability in a physiologic signal of a patient 1302. In general, the system 1300 senses and records a physiologic signal of a patient, and processes the sensed physiologic signal, for example, to determine a cardiac state for the patient. The processing may be performed within the sensing device 1304, within the external equipment, or partially within the sensing device 1304 and partially in the external equipment. Cardiac state information can also be displayed for review by a health care professional 1310 to look at long term issues. Similarly, the patient's cardiac state information can be transmitted to a device to alert the patient or the health care professional 1310 that a severe cardiac event is likely and that the patient needs immediate medical attention.

In FIG. 13, a patient 1302 is shown as having the sensing device 1304 implanted in a subcutaneous pocket beneath the patient's skin. In other implementations, the sensing device 1304 can be implanted such that leads extend into the patient's 1302 heart. In still other implementations, the sensing device 1304 is an external device. The sensing device 1304 is capable of wirelessly transmitting information (either the raw physiologic signal data or information derived from processing the physiologic signal data) through a network 1306 such as the Internet, so that the information can be provided to a remote server 1308. In some implementations, the sensing device 1304 telemeters data to an intermediate external device, such as a base station unit in the patient's home, and the intermediate external device sends the data over the network 1306 to the external processing equipment (e.g., server 1308).

The system 1300 can process a sensed physiologic signal by performing harmonic decomposition. In some implementations, physiologic signal data can be transmitted through various devices via telemetry (e.g., communication via telephone lines or other data lines, communication via a wireless link, and the like) before reaching the server 1308. As described further below, the server 1308 may include software modules, hardware modules, or both, that can be used to perform various forms of signal processing on the physiologic signal data to determine the status of the patient's 102 cardiac state. For example, the server 1308 can isolate a portion of the patient's 102 heartbeats using harmonic decomposition of the physiologic signal data. The server 1308 can use various techniques to implement the harmonic decomposition, including filter banks or a phase-locked loop.

After sensing the physiologic signal data, the sensing device 1304 can store a sample of the physiologic signal data in internal memory. In some implementations, the implanted device may not record until a specified event has been triggered. In alternative implementations, the sensing device 1304 can process the physiologic signal data to determine the patient's 1302 cardiac state. For example, the implanted device can perform harmonic decomposition on the physiologic signal data and transmit the results to the monitoring device 1312 (e.g., over the network 1306 via the server 1308, and perhaps one or more intermediate external devices). Alternatively, the sensing device 1304 can receive the physiologic signal data and transmit the physiologic signal data without storing any of the data.

The monitoring device 1312 is shown as receiving the determinations arising from the physiologic signal data to display for the health care professional 1310. The monitoring device 1312 can include a computer program that displays the data from the server 1308 graphically on a display device. For example, the monitoring device 1312 may show a color-coded graph that tracks the determinations based on physiologic transmissions for a predetermined period of time. Similarly, the monitoring device 1312 can display other cardiac state information including morphology of the physiologic signal data or other risk markers. Alternatively, the monitoring device 1312 can display the data using numeric or text-based means. For example, the server 1308 can send an e-mail to the health care professional 1310 when an issue arises, enclosing a numeric reading regarding the patient's 1302 cardiac state. Similarly, the monitoring device 1312 may signal a change in the patient's cardiac state using a warning sound or a display of lights to alert the health care professional 1310. The monitoring device 1312 is shown as a computer in FIG. 13. However, the monitoring device 1312 can be a hand-held device, such as a mobile phone or personal data assistant. The monitoring device 1312 can also be a device worn by the patient 1302 externally.

A number of implementations of the invention have been described. Nevertheless, it will be understood that various modifications may be made without departing from the spirit and scope of the methods, systems, and devices described herein. For example, the sensing device may be a stationary device, according to some implementations. The sensing device may be used in implementations where data is collected in a health care facility, such as a hospital. The sensing device can transmit data to be analyzed using the techniques disclosed herein. In implementations that use an implantable device, the implanted device may comprise two or more implantable enclosures. In some implementations, an alternans indicator value derived from an electrical signal may be used in combination with an alternans indicator value derived from a mechanical signal to assess a patient's cardiac state.

Using the methods described herein, efficient time-frequency analysis techniques can be used to extract components of a physiologic signal, such as a repolarization signal. In some implementations, frequencies other than fractional and integer harmonics can be used in determining an alternans indicator. Using the methods described herein, efficient time-frequency analysis techniques can be used to extract components of a physiologic signal, such as a repolarization signal. In some implementations, other wavelets could be used to decompose the physiologic signal, such as to decompose the repolarization signal. Accordingly, other implementations are within the scope of the following claims.

What is claimed is:

1. A method of determining a cardiac condition, the method comprising:
    receiving a sensed physiologic signal for a period of time including multiple cardiac cycles;
    determining, by a processing module using the received physiologic data, a heart beat frequency to be used as a reference frequency;
    extracting, by the processing module, a plurality of harmonics of the received physiologic signal based on the reference frequency, wherein the harmonics correspond to a plurality of alternans frequencies and include integer harmonics and fractional harmonics, and wherein the harmonics are extracted using one or more band pass filters, and further comprising assembling a blended signal comprising a sum of corresponding integer and fractional harmonics; and
    determining, by the processing module, amplitudes of at least some of the extracted harmonics and using the amplitudes to determine an alternans indicator value indicative of a patient's susceptibility to a cardiac condition or to a cardiac event, and storing the alternans indicator value in an electronic storage location.

2. The method of claim 1, wherein the sensed physiologic signal is an ECG signal.

3. The method of claim 2, wherein the harmonics are extracted from a repolarization component of the ECG signal.

4. The method of claim 3, wherein the repolarization component is a continuous repolarization component of the ECG signal.

5. The method of claim 4, wherein the alternans indicator value is a T-wave alternans amplitude.

6. The method of claim 1, further comprising computing a complex envelope of the blended signal.

7. The method of claim 1, wherein the sensed physiologic signal is collected by an implanted device.

8. The method of claim 7, wherein the implanted device collects the sensed physiologic signal using at least two electrodes positioned subcutaneously within a patient.

9. The method of claim 7, wherein the implanted device collects the sensed physiologic signal using at least one intracardiac electrode.

10. The method of claim 7, wherein the sensed physiologic signal is telemetered from the implanted device to external processing equipment.

11. The method of claim 10, wherein the processing module is within the external processing equipment.

12. The method of claim 7, wherein the sensed physiologic signal is analyzed within the implanted device.

13. The method of claim 7, wherein the processing module is within the implanted device.

14. The method of claim 1, wherein the physiologic signal is an electrocardiogram or electrogram, and wherein the alternans indicator value is a QRS alternans value.

15. The method of claim 1, further comprising issuing a warning in response to comparing the alternans indicator value to the predetermined threshold value.

16. The method of claim 1, wherein input noise associated with the sensed physiologic signal is measured, and wherein at least a portion of the sensed physiologic signal is rejected if the measured noise exceeds a predetermined threshold.

17. The method of claim 1, further comprising comparing the alternans indicator value to a predetermined threshold value and storing a result of the comparison in another electronic storage location.

18. A method of determining a cardiac condition, the method comprising:
receiving a sensed physiologic signal for a period of time including multiple cardiac cycles;
determining, by a processing module using the received physiologic data, a heart beat frequency to be used as a reference frequency;
extracting, by the processing module, a plurality of harmonics of the received physiologic signal based on the reference frequency, wherein the harmonics correspond to a plurality of alternans frequencies and include integer harmonics and fractional harmonics, and wherein the harmonics are extracted using one or more band pass filters, and further comprising normalizing one or more powers of the extracted harmonics by a power of the noise band; and
determining, by the processing module, amplitudes of at least some of the extracted harmonics and using the amplitudes to determine an alternans indicator value indicative of a patient's susceptibility to a cardiac condition or to a cardiac event, and storing the alternans indicator value in an electronic storage location.

19. A method of determining a cardiac condition, the method comprising:
receiving a sensed physiologic signal for a period of time including multiple cardiac cycles;
determining, by a processing module using the received physiologic data, a heart beat frequency to be used as a reference frequency;
extracting, by the processing module, a plurality of harmonics of the received physiologic signal based on the reference frequency, wherein the harmonics correspond to a plurality of alternans frequencies, wherein each of the plurality of harmonics are fractional harmonics; and
determining, by the processing module, amplitudes of at least some of the extracted harmonics and using the amplitudes to determine an alternans indicator value by taking the square root of a summation of powers of amplitudes of the extracted fractional harmonics, wherein the alternans indicator value is indicative of a patient's susceptibility to a cardiac condition or to a cardiac event, and storing the alternans indicator value in an electronic storage location.

20. A method of determining a cardiac condition, the method comprising:
receiving a sensed physiologic signal for a period of time including multiple cardiac cycles;
determining, by a processing module using the received physiologic data, a heart beat frequency to be used as a reference frequency;
extracting, by the processing module, a plurality of harmonics of the received physiologic signal based on the reference frequency, wherein the harmonics correspond to a plurality of alternans frequencies and include integer harmonics and fractional harmonics, and wherein the harmonics are extracted using one or more band pass filters, wherein alternans signal morphology is reconstructed from the fractional harmonics; and
determining, by the processing module, amplitudes of at least some of the extracted harmonics and using the amplitudes to determine an alternans indicator value indicative of a patient's susceptibility to a cardiac condition or to a cardiac event, and storing the alternans indicator value in an electronic storage location.

21. A system, comprising:
an electrode configured to sense a physiologic signal of a patient for a period of time including multiple cardiac cycles; and
a processor module programmed to:
receive the sensed physiologic signal;
determine, using the received physiologic data, a heart beat frequency to be used as a reference frequency;
extract a plurality of harmonics of the received physiologic signal based on the reference frequency, wherein the harmonics correspond to a plurality of alternans frequencies and include integer harmonics and fractional harmonics;
assemble a blended signal comprising a sum of corresponding integer and fractional harmonics; and
determine amplitudes of at least some of the extracted harmonics and use the amplitudes to determine an alternans indicator value indicative of a patient's susceptibility to a cardiac condition or to a cardiac event.

22. The system of claim 21, wherein the sensed physiologic signal is an ECG signal.

23. The system of claim 22, wherein the harmonics are extracted from a repolarization component of the ECG signal.

24. The system of claim 21, wherein the alternans indicator value is a T-wave alternans amplitude.

* * * * *